United States Patent
Schäfer et al.

(10) Patent No.: US 7,202,055 B2
(45) Date of Patent: Apr. 10, 2007

(54) PROCESS FOR THE PRODUCTION OF PROTEINS AND THE PRODUCTION OF ARRAYS OF PROTEINS

(75) Inventors: Klaus Peter Schäfer, Constance (DE); Ingeborg Mühldorfer, Constance (DE)

(73) Assignee: Altana Pharma AG, Constance (DE)

( * ) Notice: Subject to any disclaimer, the term of this patent is extended or adjusted under 35 U.S.C. 154(b) by 168 days.

(21) Appl. No.: 10/399,954

(22) PCT Filed: Dec. 19, 2001

(86) PCT No.: PCT/EP01/15008

§ 371 (c)(1),
(2), (4) Date: Jul. 25, 2003

(87) PCT Pub. No.: WO02/50260

PCT Pub. Date: Jun. 27, 2002

(65) Prior Publication Data

US 2004/0023329 A1 Feb. 5, 2004

Related U.S. Application Data

(60) Provisional application No. 60/256,456, filed on Dec. 20, 2000, provisional application No. 60/307,166, filed on Jul. 24, 2001.

(51) Int. Cl.
*C12N 1/00* (2006.01)
*C12N 15/74* (2006.01)
*C12N 15/79* (2006.01)
*C12M 1/00* (2006.01)
*C12P 21/00* (2006.01)

(52) U.S. Cl. .................. 435/69.1; 435/383; 435/288.4; 435/70.1; 435/395

(58) Field of Classification Search ............... 435/69.1, 435/325, 252.33, 254.23
See application file for complete search history.

(56) References Cited

U.S. PATENT DOCUMENTS 5,437,998 A * 8/1995 Schwarz et al. ......... 435/298.2
6,544,788 B2 * 4/2003 Singh ........................ 435/383

FOREIGN PATENT DOCUMENTS

WO  WO 01/79849  10/2001

OTHER PUBLICATIONS

Koronakis, Vassilis, et al., "Energetically distinct early and late stages of HlyB/HlyD-dependent secretion across both *Escherichia coli* membranes". The EMBO Journal, 10: 3263-3272, 1991.

Walter, Gerald, et al., "Protein arrays for gene expression and molecular interaction screening". Current Opinion in Microbiology, 3: 298-302, 2000.

Lueking, Angelika, et al., "Protein Microarrays for Gene Expression and Antibody Screening". Analytical Biochemistry, 270: 103-111, 1999.

Gentschev, Ivaylo, et al., "Development of antigen-delivery systems, based on the *Escherichia coli* hemolysin secretion pathway". Gene, 179: 133-140, 1996.

Emili, Alia Qureshi, et al., "Large-scale functional analysis using peptide or protein arrays". Nature Biotechnology: 18, 393-397, Apr. 2000.

* cited by examiner

*Primary Examiner*—Scott D. Priebe
*Assistant Examiner*—Michael Burkhart
(74) *Attorney, Agent, or Firm*—Gary M. Nath; Joshua B. Goldberg; Charles D. Niebylski

(57) ABSTRACT

Described is a novel process for the production of at least one protein of interest by secretion of the protein of interest from a pro- or eukaryotic host cell in a compartment system, which host cell is stably expressing a secretion system and capable of heterologous secretion of the protein of interest and which compartment system has at least a first and a second compartment and wherein the host cell is located in the first compartment and wherein the first and second compartment are separated from each other by a barrier, wherein the barrier is permeable for the secreted protein of interest, but not permeable for the host cell.

16 Claims, 2 Drawing Sheets

PROCESS FOR THE PRODUCTION OF PROTEINS AND THE PRODUCTION OF ARRAYS OF PROTEINS

This application is a 371 of PCT/EP01/15008, filed Dec. 19, 2001, which claims the benefit of U.S. patent application Ser. No. 60/307,166, filed Jul. 24, 2001 and U.S. patent application Ser. No. 60/256,456, filed Dec. 20, 2000.

TECHNICAL FIELD

The present invention relates to a process for the production and purification of proteins of interest by secretion of the protein of interest from a host cell in a compartment system, to a process for the production of protein arrays, to a suitable compartment system and to host cells and plasmids suitable for the production and secretion of the proteins of interest.

PRIOR ART

The current technology on the creation of protein and proteome arrays is based upon cloning of open reading frames (ORFs) encoding certain proteins of interest into expression vectors and their expression by corresponding bacterial cells carrying the respective vectors. Following a gentle lysis of the bacteria on filters, the bacterial debris is washed off, and the filter-bound proteins are utilized for binding studies. [Büssow et al. (1998) Nucl. Acids Res. 26:5007–5008; Walter et al. (2000) Curr. Op. Microbiol. 3:298–302]. The drawbacks of this method are (i) that due to the fact that all proteins produced by these bacteria are present on the filter, there is a high background of bacterial proteins which can interfere with specific binding studies, and (ii) that the proteins of interest may be denatured during bacterial lysis. The problem of a high background level can be solved by purification of the overexpressed proteins, however, this is very labour intensive.

Surprisingly it was found now, that the drawbacks of the current technology can be avoided by a novel process which make use of a secretion system which ensures the secretion of a protein of interest from a host cell in a compartment system which allows the separation of the protein of interest form its synthesizing host cell and its components and allows the preservation of the protein of interest in an undenatured form.

DESCRIPTION OF THE INVENTION

A first subject of the present invention is therefore a process for the production of at least one protein of interest by secretion of the protein of interest by a host cell into a compartment system, which host cell is stably expressing a secretion system and capable of heterologous secretion of the protein of interest and which compartment system has at least a first and a second compartment and wherein the host cell is located in the first compartment and wherein the first and second compartment are separated from each other by a barrier, wherein the barrier is permeable for the secreted protein of interest, but not permeable for the host cell. Optionally the protein of interest is retained in the second compartment and may be collected from the second compartment. This novel process ensures the secretion of the proteins of interest into a compartment system which allows their separation from the synthesizing host cell and all of its components and preserves the proteins in a non-denatured form as no lysis of the host cell is necessary. As an option the novel process allows the retention of the secreted protein on a carrier and/or purification by use of an affinity tag, and as further option allows their detection by use of an epitope-tag and as another option allows the removal of secretion signal and tag sequences which might affect the function of the protein of interest by introduction of suitable protease cleavage sites.

Another subject of the present invention is a process for the production of a protein array. In connection with the invention the term protein array refers to an ordered arrangement of individual proteins of interest, in particular to an ordered arrangement of individual proteins, allowing the parallel analysis of the proteins. Preferentially the organisational principle is partitioning, using either tubes, cavities or discrete patches or spots on planar surfaces [Walter et al. (2000) Curr. Op. Microbiol. 3:298–302]. The invention allows the secretion of a protein of interest from a host cell which grows in one component of a compartment system into another component of the same compartment system. The host cells are expressing a secretion system, which enables the host cells to secrete heterologous proteins of interest. The compartment system has at least a first and a second compartment, wherein the different host cells are arranged in an array form in said first compartment and wherein the first and second compartment are separated from each other by a barrier, wherein the barrier is permeable for the secreted proteins of interest, but not permeable for the host cell and its other components and wherein the secreted proteins of interest are received in the second compartment in the form of an array.

A still further subject of the invention is a protein array obtainable by a process according to the present invention. Such array will only contain proteins secreted by the host cell constructs.

Protein of interest in connection with the present invention refers to any protein of an organism of interest, which may be of viral, prokaryotic or eukaryotic nature, which can be secreted by a suitable secretion system.

Secretion of the protein of interest from a host cell in connection with the invention refers to the transport of the protein of interest form the producing host cell into the extracellular space.

Secreted protein in connection with the invention refers to any protein of interest which can be secreted by a suitable secretion system, in particular to a protein of interest secreted as a fusion protein with the C-terminal signal sequence of the *E. coli* α-hemolysin protein HlyA or with the α-factor signal sequence from *Saccharomyces cerevisiae*.

Host cell refers to any cell which is able to secrete heterologous proteins of interest in particular to apathogenic Gram-negative bacteria, preferentially to apathogenic *E.coli*, in particular *E.coli* K-12, or *Pichia pastodis* yeast cells.

Secretion system in connection with the invention refers to any prokaryotic or eukaryotic secretion system which allows the secretion of heterologous proteins of interest, in particular to either a secretion system of Gram negative bacteria [Sandkvist and Bagdasarian (1996) Curr. Op. Biotechnol. 7:505–511], preferentially to the type I secretion system of Gram negative bacteria, preferentially to the *E. coli* α-hemolysin secretion system, as described in the following publications [Dietrich et al. (1998) Nature Biotechnol. 16:181–185; Gentschev et al. (1994) Behring Inst. Mitt. 95:57–66; Gentschev et al. (1996) Mol. Gen. Genet. 252:266–274; Gentschev et al. (1996) Gene. 179:133–140; Gentschev et al. (1997) Behring Inst. Mitt. 98:103–113;

Gentschev et al. (1998) Infect. Immun. 66:2060–2064; Mollenkopf et al. (1996) BioTechniques. 21:854–860; Spreng and Gentschev (1998) FEMS Microbiol. Lett. 165:187–192; Spreng et al. (1999) Mol. Microbiol. 31:1589–1601], in particular to a modified version of the E. coli α-hemolysin secretion system, or to a secretion system of Gram positive bacteria [Braun et al. (1999) Curr. Op. Biotechnol. 10:376–381; Ferrari et al. (1993) in A. L. Sonenshein et al. (eds). Bacillus spp. and other Gram-positive bacteria. Am. Soc. Microbiol, Washington, D.C., p. 917–937.; Freudl (1992) J. Biotechnol. 23:231–240; Pozidis et al. (2001) Biotechnol. Bioeng. 72:611–619; Van Wely et al. (2001) FEMS Microbiol. Rev. 25:437–454], preferentially Bacillus spp., Staphlyococcus spp., Streptomyces spp., or to yeast secretion systems, preferentially those mediated by the Saccharomyces cerevisiae α-factor or the Pichia pastotris acid phosphatase (PHO1) signal sequence [Cereghino and Cregg (2000) FEMS Microbiol. Rev. 24:45–66; these yeast secretion systems are also commercially available from Invitrogen Corporation].

It is preferred that secretion system in connection with the invention refers to any prokaryotic or eukaryotic secretion system which allows the secretion of heterologous proteins of interest, in particular to the α-hemolysin secretion system, preferentially to the E.coli α-hemolysin secretion system, in particular to a modified version of the E. coli α-hemolysin secretion system [Dietrich et al. (1998) Nature Biotechnol. 16:181–185; Gentschev et al. (1994) Behring Inst. Mitt. 95:57–66; Gentschev et al. (1996) Mol. Gen. Genet. 252:266–274; Gentschev et al. (1996) Gene. 179:133–140; Gentschev et al. (1997) Behring Inst. Mitt. 98:103–113; Gentschev et al. (1998) Infect. Immun. 66:2060–2064; Mollenkopf et al. (1996) BioTechniques. 21:854–860; Spreng and Gentschev (1998) FEMS Microbiol. Lett. 165:187–192; Spreng et al. (1999) Moi. Microbiol. 31:1589–1601], or to a modified version of the Pichia pastoris secretion system commercially available fromInvitrogen.

In connection with the invention secretion of a heterologous protein refers to the secretion of a protein by a host cell which may not necessarily be part of the natural proteome of the host cell but is synthesized by the host cell due to the fact that the corresponding gene was introduced into the host cell genome. In connection with the invention secretion of the respective heterologous protein by the host cell refers to its transport from the host cell into the extracellular space by a secretion machinery, in particular as a fusion between the heterologous protein of interest and the C-terminal HlyA signal sequence by the α-hemolysin secretion system or the Saccharomyces cerevisiae α-factor or the Pichia pastoris acid phosphatase (PHO1) signal sequence.

Host cell stably expressing a secretion system and capable of heterologous secretion of the protein in connection with the invention refers to a host cell which is able to express a secretion system that is capable of inducing the secretion of a protein, the corresponding gene of which was introduced into its genome. In particular, capable of heterologous secretion of the protein refers to the capability to secrete a heterologous protein. The stable expression of the secretion system can be acchieved by assuring that the secretion system is chromosomally encoded, which can be the case either by nature or due to genetic engineering. It is also preferred that for stable expression of the secretion system components of the secretion system are cloned on a mobile vector, e.g. plasmid, also encoding the heterologous proteins of interest to be secreted. It is also preferred that for stable expression of the secretion system the secretion system and the heterologous protein of interest are cloned on separate, compatible mobile vector, e.g. plasmids.

In the following, a prokaryotic secretion system, based on the E. coli α-hemolysin secretion system and a eukaryotic secretion system, based on a Pichia pastoris secretion system, will be described:

Prokaryotic Secretion System

Prokaryotic secretion system refers to the application of a prokaryotic cell as a host cell for the secretion of a heterologous protein of interest, in particular to either apathogenic Gram-negative bacteria, preferentially to apathogenic E. coli, in particular E. coli K-12 or B strains, or apathogenic Gram-positive bacteria, preferentially Bacillus spp., Staphlyococcus spp., Streptomyces spp.

In connection with the invention, secretion of the respective heterologous protein by a prokaryotic host cell refers to its transport from the prokaryotic host cell into the extracellular space by a secretion machinery.

Prokaryotic E. coli α-hemolysin Secretion System

The α-hemolysin is a pathogenicity factor which is frequently produced by extraintestinal E. coli pathogens, predominantly by uropathogenic E. coli (UPEC). It is a membrane-damaging, pore-forming extracellular cytotoxin belonging to the Rtx (repeats in toxin) family of protein toxins. The HlyA protein lysis eukaryotic cells, including erythrocytes, because of which It was termed "hemolysin", but also other cells, such as granulocytes and epithelial cells. Rtx cytotoxins are produced by a variety of Gramnegative bacteria and are characterized by a C-terminal calcium-binding region with a variable number of glycine-rich repeat units consisting of nine amino acids. Calcium-binding of the released Rtx toxins in the extracellular space is essential for their cytotoxic activities. They are transported across both the inner and outer membranes of Gram-negative bacteria by the sec-independent type I secretion pathway. While in the majority of hemolytic E. coli pathogens, the hly determinants are chromosomally encoded, in about 5% of them the hly genes are located on plasmids. [Ludwig and Goebel (1991) In: Sourcebook of bacterial protein toxins, Eds. Alouf, J. E., Freer, J. H., Academic Press, pp. 117–125; Mühldorfer and Hacker (1994) Microb. Pathogen. 16:171–181].

The synthesis and secretion of the E. coli α-hemolysin is encoded by an operon consisting of four genes, designated hlyC, hlyA, hlyB and hlyD [Ludwig and Goebel (1991) In: Sourcebook of bacterial protein toxins, Eds. Alouf, J. E., Freer, J. H., Academic Press, pp. 117–125]. While hlyA codes for the structural HlyA cytolytic protein, the co-synthesized HlyC protein is required for HlyA activation within the bacterial cytosol by posttranslationally converting the nontoxic prohemolysin (proHlyA) into the toxic α-hemolysin (HlyA) by fatty acylation of two internal lysine residues [Ludwig and Goebel (1991) In: Sourcebook of bacterial protein toxins, Eds. Alouf, J. E., Freer, J. H., Academic Press, pp. 117–125; Stanley et al. (1998) Microbiol. Mol. Biol. Rev. 62:309–333; Stanley et al. (1999) Mol. Microbiol. 34:887–901; Trent et al. (1998) Biochemistry. 37:4644–4652; Trent et al. (1999) Biochemistry. 38:9541–9548]. HlyB and HlyD are required for the transport of HlyA across the bacterial membranes [Ludwig and Goebel (1991) In: Sourcebook of bacterial protein toxins, Eds. Alouf, J. E., Freer, J. H., Academic Press, pp. 117–125]. Moreover, the outer membrane protein TolC, which is chromosomally encoded and not part of the α-hemolysln operon, is part of the α-hemolysin secretion apparatus [Ludwig and Goebel (1991) In: Sourcebook of bacterial protein toxins, Eds. Alouf, J. E., Freer, J. H., Academic Press, pp. 117–125; Schlör et al. (1997) Mol. Gen. Genet. 256:306–319]. The signal sequence within the C-terminal 60 amino acids of HlyA, which contains a helix(α1)-linker-helix(α2) motif, is sufficient for being recognized by the secretion apparatus [Koronakis et al. (1989) EMBO J. 8:595–605; Jarchau et al., (1994) Mol. Gen. Genet. 245:53–60; Hul et al. (2000) J. Biol. Chem. 275:2713–2720], consisting of the membrane proteins HlyB, HlyD and TolC. The C-terminal peptide can also be secreted by itself [Jarchau et al., (1994) Mol. Gen. Genet. 245:53–60; Hui et al. (2000) J. Biol. Chem. 275: 2713–2720]. It has recently been demonstrated that only the α1-amphiphilic helix and the linker but not the second helix are essential for HlyA transport [Hui et al. (2000) J. Biol. Chem. 275:2713–2720]. HlyB, an inner membrane traffic ATPase, which energizes the transport of HlyA, recognizes the HlyA C-terminal signal sequence with its cytoplasmic domains, initiates HlyA translocation and forms a transmembrane channel in the inner membrane through which HlyA is translocated. HlyD was suggested to serve as a linker between the inner and outer bacterial membrane. It is inserted in the inner membrane, but most of it is localized in the periplasm where It was suggested to interact with both HlyB of the inner membrane and TolC of the outer membrane. By interacting with periplasmic HlyB loops, HlyD and HlyB form a channel through the periplasm. As HlyD also has a TolC-homologous part, it is assumed to participate with TolC in the formation of a transmembrane channel in the outer membrane through which HlyA is secreted. Consequently, HlyD is required for pulling HlyA through the bacterial membranes and for its release into the extracellular space. In case of the plasmid-encoded α-hemolysin, its synthesis and secretion in $E.$ $coli$ is enhanced by HlyR, a long distance activator which is encoded by the hlyR gene located at some distance upstream of the hlyC gene [Vogel et al., (1988) Mol. Gen. Genet. 212:76–84]. In contrast, a hlyR homologous activator gene has not been found in chromosomal hly determinants. [Ludwig and Goebel (1991) In: Sourcebook of bacterial protein toxins, Eds. Alouf, J. E., Freer, J. H., Academic Press, pp.117–125].

It has previously been demonstrated that the hemolysin secretion apparatus works in a great variety of Gram-negative bacteria [Spreng et al. (1998) FEMS Microbiol. Lett. 165:187–192] and that it can be utilized for the secretion of heterologous proteins of different origin (e.g. bacterial, viral, protozoan) [Dietrich et al. (1998) Nature Biotechnol. 16:181–185; Gentschev et al. (1994) Behring Inst. Miff. 95:57–66; Gentschev et al. (1996) Mol. Gen. Genet. 252:266–274; Gentschev et al. (1996) Gene. 179: 133–140; Gentschev et al. (1997) Behring Inst. Mitt. 98:103–113; Gentschev et al. (1998) Infect. Immun. 66:2060–2064; Mollenkopf et al. (1996) BioTechniques. 21:854–860; Spreng and Gentschev (1998) FEMS Microbiol. Lett. 165:187–192; Spreng et al. (1999) Mol. Microbiol. 31:1589–1601]. This was acchieved by generating gene fusions between heterologous genes and the C-terminal signal sequence of hlyA, coding for secretion-competent hybrid proteins which can be secreted when HyB, HlyD and TolC are synthesized by the respective bacteria. Thus, it was shown to be of value as an antigen delivery system for the presentation of secreted antigens by Gram-negative bacterial vaccine carriers. However, it became obvious that there are great differences in the yields of heterologous protein secretion obtained with different proteins. Thus, the efficacy of heterologous protein secretion via the hemolysin secretion system is dependend on the nature of the heterologous protein. E. g. proteins which have an N-terminal signal sequence and are usually secreted by the sec-dependent secretion pathway are only inefficiently transported by the hemolysin secretion system [Gentschev et al. (1997) Behring Inst. Mitt. 98:103–113]. However, this problem can be circumvented by optionally using a host cell harbouring a secA mutation [Gentschev et al. (1997) Behring Inst. Mitt. 98:103–113], which is a preferrred aspect in connection with the invention. Moreover, it has been demonstrated that the efficacy of heterologous protein secretion via the hemolysin secretion system correlates with the size of the heterologous gene in front of the $HlyA_s$ signal [Spreng and Gentschev (1998) FEMS Microbiol. Lett. 165:187–192]. As described below in greater detail, this problem is also faced in the invention by optionally binding the proteins of interest via an affinity tag onto a carrier with a suitable binding partner until saturation will be achieved.

Eukaryotic Secretion System

Eukaryotic secretion system refers to the application of a eukaryotic cell as a host cell for the secretion of a heterologous protein of interest, in particular to apathogenic yeasts, e.g. $Saccharomyces$ $cerevlsieae$ or $Pichia$ $pastors$. In connection with the invention, secretion of the respective heterologous protein by a eukaryotic host cell refers to its transport from the eukaryotic host cell into the extracellular space by a secretion machinery.

The yeast $Pichia$ $pastoris$ can relatively easy be genetically manipulated. As it is a eukaryotic organism, it is capable of many posttranslavional modifications which occur also in higher eukaryotes, such as proteolytic processing, protein folding, disulfide bonding and glycosylations. Thus, many eukaryotic proteins which when expressed in bacteria are stored as inactive molecules in inclusion bodies, can be produced by yeast cells as active molecules with all the necessary posttranslational modifications. Compared with higher eukaryotic cells, yeast cells offer the advantage that they grow faster and that their fermentation is easier and cheaper and that their yield of recombinant heterologous protein is higher [Cereghino and Cregg (1999) Curr. Opinion Biotechnol. 10:422–427; Dominguez et al. (1998) Int. Microbiol. 1:131–142].

$Pichia$ $pastoris$ is a methylothrophic yeast, i.e. it is able to metabolize methanol. The first step in the methanol metabolism involves the oxidation of methanol to formaldehyde. This process is catalyzed by the enzyme "Alkohol-Oxidase" (AOX). In order to prevent the toxic effect of hydrogen peroxide (a product of the enzyme reaction) for the yeast cell, the reaction takes place in a specialized organell, the so-called peroxisome. The expression of the AOX1-gene is tightly and is induced by high amounts of methanol.

The $P.$ $pastoris$ expression and secretion systems is commercially available from invitrogen. These systems utilize the AOX-promoter for the expression of heterologous genes. Culturing $P.$ $pastoris$ cells in a fermenter in the presence of methanol provides yields of recombinant proteins up to 30% of the soluble total protein content of the culture.

$P.$ $pastoris$ can produce heterologous proteins either intracellulary or it can secrete those proteins into the extracellular medium. A shuttle plasmid vector, capable of replicating in $E.$ $coli$ and integrating into the $P.$ $pastoris$ genome is provided, which can be used for the expression and secretion of heterologous proteins, as it contains a sequence encoding the α-factor-signal sequence from $Saccharomyces$ $cerevisiae$, which guarantees the efficient secretion of heterologous proteins. As $P.$ $pastoris$ secretes only very little endogenous proteins and its growth medium doesn't require proteins, the secreted heterologous protein forms the main secretion product of a *P. pastoris* culture [Bretthauer und Castellino (1999) Biotechnol. Appi. Biochem. 30:193–200; Buckholz and Gleeson (1991) Bio/Technology 9:1067–1072; Cereghino and Cregg (1999) Curr. Opinion Biotechnol. 10:422–427; Cereghino and Cregg (2000) FEMS Microbiol. Rev. 24:45–66; Cregg et al. (2000) Mol. Biotechnol. 16:23–52; Dominguez et a. (1998) Int. Microbiol. 1:131–142; Gleeson et al. (1998) in: Methods in Mol. Biol. 103: *Pichia* Protocols:81–94; Stratton et al. (1998) In: Methods in Mol. Biol. 103: *Pichia* Protocols:107–120].

The *P. pastoris* secretion system can be used in connection with the present invention. Therefore, in analogy to the above described *E. coli* hemolysin secretion system, plasmids derived from the above mentioned *Pichia pastoris* vectors can be constructed, harbouring various genes of interest and optional various protease cleavage sites and tag sequences.

The compartment system according to the invention has at least a first and a second compartment separated by a barrier. Preferably compartment system refers to a system consisting of two locally partitioning subsets, the first of which harbours the growing host cell either in liquid growth medium or on a planar surface, and the second of which is separated from the first subset by a barrier which allows the flow of proteins produced and secreted by the host cell from the first into the second subset but prevents host cell migration.

Barrier refers to a means of partitioning two components of a compartment system selectively preventing the flow-through of certain objects from the first into the second component in particular, barrier refers to a means of partitioning two compartments of a compartment system, allowing the flow-through of proteins but retains other host cell debris, in particular It refers to a membrane, preferably to a filter. In a preferred embodiment of this invention, a barrier partitioning two compartments of a compartment system is part of the first compartment.

Examples for suitable compartmental systems are (i) a double filter system on a bacterial growth agar plate with bacterial colonies on the top and secreted proteins on the bottom filter, as shown in FIG. 1 and as described in principle for the detection of Shiga-like toxin-producing *E. coli* in fecal samples [Hull et at. (1993) J. Clin. Microbiol. 31:1167–1172], (ii) a system consisting of different filter-separated compartments containing liquid host cell cultures in one compartment and secreted protein solutions in the other compartment. Those two compartments are separated by a membrane that prevents host cell migration but allows diffusion of proteins along their concentration gradient. On a small scale, e. g. this can be realized in form of a system consisting of stacked microwells which are separated by a membrane that prevents bacterial migration but allows diffusion of proteins along their concentration gradient, as illustrated in FIG. 2. In the latter case, the top wells may contain host cell cultures which secrete fusions between the protein of interest and a suitable signal sequence (e. g. *E. coli* HlyA$_s$- or the yeast α-factor) as described above. While the host cells are forced by the filter to remain in the top well, the secreted protein solutions diffuse into the bottom wells and can be harvested as a protein solution. In case of the double filter technology, the top filter has to have a pore diameter that prevents bacterial migration from the top to the lower filter, but allows flow of the secreted fusion proteins to the lower filter. Preferably it should have a low protein binding capacity. In contrast, the lower filter has to have an optimal protein binding capacity, either by nature or as a consequence of being coated at certain spots with a component (e. g. single stranded nucleic acids) which is an optimal binding partner for a component (e. g. C-terminal domain of A1 protein, [Cartegni et al. (1996) J. Mol. Biol. 259:337–348] of the protein fusion to be secreted by the bacteria growing on the top filter. Both filters must allow the flow-through of nutrients and growth factors from the bacterial growth agar plate to the bacterial colonies growing on the top filter. In case of the technology using different, filter-separated compartments containing liquid bacterial cultures in one compartment and secreted protein solutions in the other compartment (e. g. stacked microwells separated by a filter), the separating filter has to have a pore diameter that prevents bacterial migration but allows flow of the secreted fusion proteins.

Prokaryotic System: Construction of a Gram Negative Bacterial Strain for Heterologous Protein Secretion Based in the *E coli* α-hemolysin Secretion System In connection with the invention, the hlyB and hlyD genes are introduced into the Gram-negative bacterial genome, harbouring a chromosomally encoded tolC gene, in order to enable the bacteria to express the complete α-hemolysin secretion apparatus. In connection with the invention, proteins of interest are made competent for secretion via the α-hemolysin secretion system by the creation of gene fusions between the respective heterologous genes of interest and the C-terminal signal sequence of HlyA (hlyA$_s$). The gene fusions are cloned on suitable mobile vectors, such as plasmids or cosmids. Consecutively, they are introduced into a Gram negative bacterial strain which expresses the complete α-hemolysin secretion apparatus, consisting of HlyB, HlyD and TolC. The stable expression of the secretion system can be acchieved by insertion of the hlyB and hlyD genes into the bacterial chromosome. Alternatively, the hlyB and hlyD genes can be cloned on a mobile vector, e. g. plasmid, also encoding the heterologous proteins of interest as a fusion with the HlyA signal sequence. As another option, the hlyB and hlyD genes and the fusion between the gene encoding the heterologous protein of interest and hlyA$_s$ can be cloned on separate, compatible plasmids.

The secreted proteins are useful for the production of protein arrays by their binding onto a carrier, optionally via an affinity tag. As an additional or alternative option, an epitope tag sequence may be included for easy detection of the secreted protein of interest. Moreover, in order to avoid loss of function of the protein of interest, optionally it might be useful to remove the HlyA-secretion signal and tag sequences by protease treatment. Therefore, as an option, the corresponding affinity and/or epitope tag sequences and protease restriction sites shall be cloned downstream of the heterologous gene of interest.

In connection with the invention it is an option to introduce the hemolysin secretion apparatus into a Gram negative bacterial strain carrying a secA mutation. This is of particular advantage in connection with the secretion of proteins which are usually secreted by the Sec-dependent secretion pathway and have an N-terminal signal sequence which are only inefficiently transported by the hemolysin secretion system [Gentschev et al. (1997) Behring Inst. Mitt. 98:103–113].

As an option, the secreted proteins may be used for the production of protein arrays with dots of single proteins, preferentially with dots of equal amounts of single proteins, the latter of which may be acchieved by binding of the proteins of interest onto a carrier, optionally via an affinity tag which is able to bind to a suitable partner spotted in equal concentrations on each spot of the array. In case of the double filter technology, saturated binding of the affinity tag bound to a protein of interest secreted from a host cell growing on the upper filter to its binding partner on the lower filter will ensure binding of equal amounts of heterologous proteins to the lower filter. Alternatively, in case of using a system consisting of different filter-separated compartments containing liquid bacterial cultures in one compartment and secreted protein solutions in the other compartment, as it can be realized e. g. in form of a stacked microwell technology, the concentrations of the secreted proteins collected in the bottom wells may be quantified. As an additional or alternative option, an epitope tag sequence may be included for easy detection of the secreted protein of interest. Moreover, in order to avoid loss of function of the protein of interest, optionally it might be useful to remove the HlyA-secretion signal and tag sequences by protease treatment. Therefore, as an option, the corresponding affinity and/or epitope tag sequences and protease restriction sites shall be cloned on the vector encoding the heterologous gene of interest.

a) Construction of a Gram Negative Bacterial Strain With a Chromosomally Encoded Hemolysin Secretion Apparatus Another subject of the invention is the construction of a Gram-negative bacterial strain, optionally an *E. coli* strain, harbouring the hemolysin secretion system genes hlyB and hlyD within the bacterial chromosome.

In order to create an *E. coli* strain which stably expresses the α-hemolysin secretion apparatus the hlyB and hlyD genes can be integrated into the bacterial chromosome of an *E. coli* strain, in particular into the secA *E.coli* mutant strain KL320. Therefore, as explained in greater detail in the experimental section, plasmid pLacHlyBD may be constructed by the following cloning procedure: The □-pir-dependent suicide plasmid pJRLacZins, (gift of Joachim Reidl, University of Würzburg), containing an EcoRV restriction site within a cloned lacZ gene, is digested with the restriction enzyme EcoRV. Consecutively, the hlyBD genes are amplified by PCR from cosmid pCOS10 and ligated with the EcoRV restricted plasmid pJRLacZins to create plasmid pLacHlyBD. The plasmid encoded lacZ gene is destroyed during this cloning procedure. Plasmid pLacHlyBD allows the integration of the hlyBD into the chromosomal lacZ gene of any *E. coli* strain or other bacterial strain harbouring a homologous lacZ gene. The chromosomal lacZ gene in *E. coli* strains not possessing the p-protein, encoded by the pir gene, is being destroyed following the introduction of plasmid pLacHlyBD and a double-crossover event between the lacZ sequences on plasmid pLacHlyBD and the chromosomal lacZ gene, in consequence of which, the hlyB and hlyD genes are being inserted into the chromosomal lacZ gene.

b) Construction of a Plasmid Carrying a Gene Fusion Between a Gene Encoding a Protein of Interest and the 3'-end of HlyA, Encoding the Signal Sequence of the HlyA Protein A still further subject of the invention is a plasmid carrying a gene fusion between a gene encoding a protein of interest and the 3'-end of hlyA, encoding the signal sequence of the HlyA protein, which allows the export of the fusion protein, and optionally carrying a protease cleavage site, affinity tag and/or epitope tag.

As mentioned above, proteins of interest can be made competent for secretion via the α-hemolysin secretion system by the creation of gene fusions between the respective heterologous genes, coding for the proteins of interest, and the C-terminal signal sequence of hlyA. The gene fusions can be cloned on suitable mobile vectors, including plasmids, and can consecutively be introduced into a Gram negative bacterial strain which stably expresses the complete α-hemolysin secretion apparatus.

Spreng and Gentschev (1998) [Spreng and Gentschev (1998) FEMS Microbiol. Left. 165:187–192; Spreng et al. (1999) Mol. Microbiol. 31:1589–1601] showed that the efficacy of heterologous protein secretion via the hemolysin secretion system correlates with the size of the heterologous gene in front of the HlyA$_s$ signal. As in the present invention, the HlyA$_s$-fusion protein secreting bacterial strains shall optionally be used for the creation of protein arrays, harbouring equal amounts of proteins dots, as an option, along with the cloning of the heterologous gene of interest, the cloning of an affinity tag (e. g. C-terminal domain of the hnRNA-binding protein A1; [Cartegni et al. (1996) J. Mol. Biol. 259:337–348]) in front of the HlyA$_s$ signal, which is able to bind to a suitable partner (e. g. single stranded nucleic acids in case of A1) spotted in equal concentrations on each spot of the array, may be included. In case of the double filter technology, saturated binding of the affinity tag to its partner on the lower filter will ensure concomitant binding of equal amounts of heterologous proteins. Alternatively, in case of using a system consisting of different filter-separated compartments containing liquid bacterial cultures in one compartment and secreted protein solutions in the other compartment, as it can be realized e. g. In form of a stacked microwell technology, the concentrations of the secreted proteins collected in the bottom wells may be quantified. Moreover, as another option, the cloning of an epitope-tag (e. g. His-tag) can be included, facilitating the detection of the resulting fusion protein. As another option, suitable protease cleavage sites should be introduced which allow the removal of the secretion signal and tag sequences that might affect the function of the protein of interest.

c) Construction of a Gram Negative Bacterial Strain Which is Able to Secrete a Heterologous Protein of Interest A still further subject of the invention is the construction of a Gram-negative bacterial strain, optionally an *E. coli* strain, harbouring the hemolysin secretion system genes hlyB and hlyD within the chromosomal lacZ gene transformed with a plasmid carrying a gene fusion between a gene encoding a protein of interest and the 3'-end of hlyA, encoding the HlyA protein which allows the export of the fusion protein and optionally carrying a protease cleavage site, affinity tag and/or epitope tag.

Following the construction of the vector harbouring a fusion between the protein of interest and the C-terminal Hly$_s$ sequence as well as optionally also an affinity tag and/or an epitope tag and a protease cleavage site, transformation of the above described α-hemolysin-secretion apparatus harbouring host strain results in the final bacterial construct.

Eukaryotic System: Construction of *Pichia pastoris* Strains for Heterologous Protein Secretion The above described *P. pastoris* secretion system can be used in connection with the present invention. In analogy to the above described *E. coli* hemolysin secretion system, plasmids derived from the above mentioned *Pichia pastoris* vectors can be constructed, harbouring various genes of interest and optional various protease cleavage sites and tag sequences.

For the production of proteome arrays which are supposed to harbour each protein of a certain organism, each protein of this organism shall be secreted. Therefore, for each protein to be secreted, each of the corresponding genes has to be fused either with the C-terminal signal sequence of hlyA or the α-factor signal and cloned onto a separate vector (e. g. plasmid) which has to be transformed into either the α-hemolysin secretion apparatus expressing bacterial strain or into a *Pichia pastoris* strain. I. e. the total amount of open reading frames of a certain organism, the proteome of which shall be investigated, will reflect the amount of bacterial constructs required for full coverage of a proteome of a certain organism.

Utility

Consequenly, this technology allows in particular the production of arrays harbouring a partial or a complete proteome of an organism for example as an array of single spots, each of which can be saturated with a single protein for example in an undenatured form or as an alternative the production of solutions consisting of specific secreted, filtered proteins. Such proteins in particular such arrays can be—directly without further purification of the proteins— used for the identification of protein binding partners of different chemical nature, including other proteins, nucleic acids, lipids, carbohydrates or other ligands. In case of the production of array-bound proteins, studies with soluble binding partners can be performed directly on the respective array (e. g. filter). In case of the production of protein solutions, binding studies can be performed either with array-bound binding partners or with soluble binding partners. Thus, such array is applicable for all conceivable binding studies, including antibody binding studies and studies on the binding of pharmaceutical compounds with array-bound target proteins. In addition, the impact of pharmaceutical compounds on the binding behaviour of other molecules can be studied. Moreover, in case of the production of protein solutions, the respective proteins can be utilized for numerous studies. E. g. they can be analyzed for their structural nature and biochemical function, e. g. in enzymatic test systems, or can be used as antigens for the creation of specific antibodies.

As the array is suitable for testing pharmaceutical drug candidates for their protein binding capacities and their impact on the binding and enzymatic capacities of other molecules, the present invention is valuable for the elucidation of mechanisms of action of the respective pharmaceutical compounds.

For the production of proteome arrays which are supposed to harbour each protein of a certain organism, each protein of this organism shall be secreted. Therefore, for each protein to be secreted, each of the corresponding genes has to be fused either with an appropriate signal sequence as described above (e. g. *E. coli* HlyA$_s$- or the yeast α-factor) and cloned onto a separate mobile vector (e. g. plasmid) which has to be transformed into the appropriate secretion system carrying host cell. i. e. the total amount of open reading frames of a certain organism, the proteome of which shall be investigated, will reflect the amount of bacterial constructs required for full coverage of a proteome of a certain organism. It is conceivable to create two kinds of those vectors for each proteome to be investigated: (i) vectors encoding an affinity tag for retainment of the fusion proteins on a protein array and (ii) vectors encoding an epitope tag for facilitated detection of the fusion proteins. Thus, studies on the interaction of proteins produced by a certain organism could be performed by binding all proteins, encoded on an "affinity tag-vector" via affinity tag onto an array, overlaying this array with a solution containing a protein encoded on an "epitope tag-vector" and detecting the interaction between the array-bound and soluble proteins via the epitope tag.

EXPERIMENTAL

Material—M dia, Chemicals, Enzymes, and Ligonucleotides

Bacteria were grown either in liquid Luria-Bertani (LB) or Minimal M9 medium, the latter of which was supplemented with 1% casaminoacids or on LB-agar or M9+1% casaminoacids-agar plates or either on Columbla-agar plates with sheep-blood or on enterohemolysin-agar plates with blood, the two latter of which were provided by Oxold (Wesel, Germany). Strains carrying recombinant plasmids were cultivated under selective antibiotic pressure. The antibiotic concentrations were dependent on the copy number of the respective plasmids (10 to 100 µg/ml). In some experiments, sucrose at a concentration of 5% and/or 10 ml/l 2% X-Gal (5-Bromo4Cholor-3-indolyl-β-galaktoside in dimethyl formamide) solution was added to the bacterial growth medium. Chemicals were purchased by Merck (Ismaning, Germany), Quiagen (Hilden, Germany), Promega (Mannheim, Germany) or Sigma (Deisenhofen, Germany) unless stated otherwise. Restriction enzymes were purchased by Amersham-Pharmacia (Freiburg, Germany). Taq DNA polymerase and other chemicals used for polymerase chain reactions (PCR) were obtained from Gibco BRL, (Karlsruhe, Germany), Boehringer (Ingelheim, Germany) or Eurogentec (Köln, Germany). The oligonucleotides used as primers for PCR are purchased from interactiva (Ulm, Germany).

Bacterial Strains, *Pichia pastoris* Strains, Plasmids, Cosmids, Oligonucleotides and Antibodies The *Pichia pastods* strains are commercially available from invitrogen. The oligonucleotides used as primers for PCR are listed in Table 1 and were purchased from interactiva (Ulm, Germany). Antibodies were obtained from different sources and are stated in the results section.

Filter Material and Filter Apparatus

The membrane filters used in the preliminary experiments of this invention were provided by Millipore (Eschborn, Germany) or Sartorius (Göttingen, Germany). They consisted either of nitocellulose, mixed cellulose esters or polyvinylidendifluorid. The filters used for a certain experiment are mentioned in the results section.

The "MultiScreen Assay System" provided by Millipore (Eschborn, Germany) was used for the proof of principle of the "stacked microwells technology".

Meth Ds

Determination of Hemolysin Production of Various *E. coli* Strains

The hemolytic activity of *E. coli* strains was tested by cultivation of those strains on blood agar plates provided by Oxoid. Hemolytic *E. coli* strains elicited a clear hemolytic zone around the bacterial colonies (Mühidorfer et al., 1996).

The uropathogenic *E. coli* strain 536, its isogenic mutant 536–21 which has lost the pathogenicity islands (Pais) I and II, each of which carries a hemolysin operon, [Berger et al. (1982) J. Bacteriol. 152:1241–1247; Blum et al. (1994) Infect. Immun. 62:606–614; Hacker et al. (1983) J. Bacteriol. 154:11145–1154], the hly-negative mutant 536–39–192 [deposited with Jörg Hacker at the University of Würzburg, Germany and with Inge Mühidorfer, Department of Molecular Biology at Byk Gulden, Konstanz, Germany] and 15 other *E. coli* strains (K-12 wt [deposited with the American Typ Culture collection (ATCC) no. 29425], JM109 [deposited with ATCC no. 53323], DH1 [deposited with ATCC no.

33849], LE392 [deposited with ATCC no. 33572], W678 [deposited with the German strain collection (DSM) no. 6968], 35 [Smith and Linggood (1971) J. Med. Microbiol. 4:467–485], J53 [Taylor (1983) Microbiol. Rev. 47:46–83.], EN99 [Blum. (1994) Dissertation, University of Würzburg, Germany] WK6 [deposited with ATCC no. 47078], HB101 [deposited with ATCC no. 33694], 5K [deposited with the *E. coli* Genetic Stock Center (CGSC) no. 5581], CC118 [Manoil and Beckwith (1985) Proc. Nati. Acad. Sci USA 82:8129–8133], C600 [deposited with ATCC no. 23724], MC1029 [Casadaban and Cohen (1980) J. Mol. Biol. 138: 179–207], DH5α [deposited with CGSC no. 7855] all of which were provided by Jörg. Hacker, University of Würzburg, Germany) were compared for their hemolytic activities on sheep blood agar plates following overnight growth. As shown in FIG. 3, only the wild-type UPEC strain 536 elicits hemolysis of erythrocytes. In a further experiment, the *E. coli* strains 536, 536–21, J53(pUCHlyCA) and J53(pUC18) were compared for their hemolytic activities on sheep blood agar plates following overnight growth. Only *E. coli* 536 and J53(pUCHlyCA) elicited hemolysis of erythrocytes.

DNA Cloning Techniques

DNA isolation, DNA cleavage with restriction enzymes, agarose gel electrophoresis, elution of DNA fragments from agarose gels, transformation of *E. coli* strains with plasmid DNA, generation of DNA probes, colony and Southern hybridization, and PCR are performed as described in "Molecular Cloning, A Laboratory Manual" [Sambrook and Russell, eds. (2001) 3$^{rd}$ ed. Cold Spring Harbor Laboratory Press, New Yorkl] and/or according to the manuals provided by the above mentioned suppliers of the corresponding kits, chemicals and enzymes.

DNA Sequencing

Sequencing of DNA, which had been isolated according to the Quiagen protocol, was performed by GATC (Konstanz, Germany), or TopLab (Munich, Germany).

Cosmid pCOS10 [Knapp et al. (1986) J. Bacteriol. 168: 22–30], kindly provided by G. Blum-Oehler, University of Würzburg, contains Pai I of the uropathogenic *E. coli* (UPEC) strain 536 [Berger et al. (1982) J. Bacteriol. 152: 1241–1247; Blum et al (1994) Infect. Immun. 62:606–614; Hacker et al. (1983) J. Bacteriol. 154:11145–1154]. Following its isolation from *E. coli* strain HB101(pCOS10), seqencing of the hemolysin operon encoded on pCOS10 was performed by GATC (Konstanz, Germany).

PAGE and Western Blot Analysis

Protein detection is acchieved by sodium dodecyl sulfate-polyacrylamide gel electrophoresis (PAGE) and consecutive Western blot analysis, using specific primary antibodies and the Promega Proto Blot alkaline phosphatase system [Sambrook and Russell, ads. (2001) Molecular Cloning, A Laboratory Manual, 3$^{rd}$ ed. Cold Spring Harbor Laboratory Press, New Yorkl; Promega manual].

Construction of an *E. coli* Strain With a Chromosomally Encoded Hemolysin Secretion Apparatus In order to create an *E. coli* strain which stably expresses the α-hemolysin secretion apparatus, a 3.6 kb DNA fragment encoding the hlyB and hlyD genes was integrated into the bacterial chromosome of various apathogenic *E. coli* strains, including K-12 wild-type, *E. coli* BL21, and J53.

The following cloning procedure was persued: Plasmid pJRLacZins, (a kind gift of Joachim Reidi, University of Würzburg), was used as a vector plasmid. It is a λ-pir-dependent suicide plasmid based on plasmid pCVD442, conferring ampicillin resistance due to the presence of the bla gene and sensitiveness against growth in the presence of 5% sucrose at a gowth temperature of 30° C. due to the presence of the sacB gene. Consequently, plasmid pCVD442 and its derivatives can only replicate in bacteria harbouring the Pir-protein, such as in the *E. coli* K-12 strains Sy327 and Sm10λpir. Plasmid pJRLacZins, which contains an EcoRV restriction site within a cloned lacZ gene, was digested with the restriction enzyme EcoRV. Consecutively, the hlyBD genes were amplified by PCR from cosmid pCOS10, using the primers StuHlyB1 and HlyD2Stu, and following restriction of the PCR product with StuI, were ligated with the EcoRV restricted plasmid pJRLacZins to create plasmid pLacHlyBD. The plasmid encoded lacZ gene was destroyed during this cloning procedure.

Plasmid pLacHlyBD allows the integration of the hlyBD genes into the chromosomal lacZ gene of any *E. coli* strain or other bacterial strain harbouring a homologous lacZ gene, as it was exemplified with the *E coli* strains K-12 wild-type, BL21, and J53. The chromosomal lacZ gene in *E. coli* strains not possessing the p-protein, encoded by the pir gene, is being destroyed following introduction of plasmid pLacHlyBD and a double-crossover event between the lacZ sequences on plasmid pLacHlyBD and the chromosomal lacZ gene, in consequence of which, the hlyB and hlyD genes is being inserted into the chromosomal lacZ gene. lacZ-negative mutants were phenotypically screened for by testing the resulting strains for growing as white colonies on agar plates containing Luria Bertani medium supplemented with 5% sucrose and X-Gal at 30° C. and for loss of ampicillin resistance. Genotypically, the mutants were tested by PCR analysis using the primers lacZEV-up and lacZEV-down. The PCR products received from the mutants differed from those of the wild-type lacZ-positive strains by size, resulting from the integration of the hlyB, hlyD sequences. Moreover, the chromosomal DNA of the putative mutants can be restricted with a restriction enzyme that does not cut within the lacZ and integrated hlyBD sequences, and can then be subjected to Southern blot analyis using a lacZ probe. Mutants differ from the wild-type lacZ-positive strains by a DNA band shift, resulting from the integration of the hlyBD sequences.

Construction of a Plasmid Harbouring a Fusion Between Genes Encoding a Protein X-HlyA$_s$-fusion Protein In order to experimentally validate the process for the production of proteins claimed in this invention, we constructed plasmid pUCHlyCA harbouring the hlyC and hlyA genes, which had been amplified by PCR, using the primers StuHlyC4 and HlyA3Stu and cosmid pCOS10 as a template, and following restriction of the PCR product with StuI, were ligated with the SmaI digested plasmid vector pUC18.

Moreover, plasmid pTOPOMycHisHlyA$_s$ was constructed. The genes encoding thrombin, Myc-epitope and His-tag were amplified by PCR using the invitrogen plasmid vector pBAD/Myc-HisA as a template and the primer ThromMycBAD which harbours the 18 bp thrombin gene sequence as a forward primer, and the HispBAD primer as a reverse primer. Cloning of the resulting 89 bp PCR product into the lacZ gene of the invitrogen vector pCR2.1.-TOPO, resulted in plasmid pTOPO-Thr-Myc-His. Consecutively, hlyA$_s$ specific sequences were amplified from pCOS10 using either the primer pairs XbaHlyA$_s$-up and XbaHlyA$_s$-down or XbaHlyA$_s$-up and XbaHlyA$_s$linker, resulting in hlyAs-specific PCR products with either 183 or 99 hlyA$_s$-specific bp and added XbaI sites, which were cloned into the XbaI site of the above described plasmid pTOPO-Thr-Myc-His.

The final plasmid constructs were termed pTOPOMycHisH-lyA$_s$-A or -B, harbouring either the 183 or 99 hlyA$_s$-specific bp, respectively.

Construction of a Gram Negative Bacterial Strain Which is Able to Secrete a Heterologous Protein of Interest In order to experimentally validate the process for the production of proteins according to the invention, plasmid pUCHlyCA was introduced into the above described hlyBD+ E. coli constructs by transformation. The resulting E. coli strains harbour a chromosomally encoded hemolysin secretion system and a plasmid encoded cytotoxin, the α-hemolysin HlyA, and toxin activator HlyC. Secretion of the HlyA cytotoxin became obvious by the hemolytic activity of the sterile-filtered (using 0,45 μm filters) culture supernatant on sheep blood agar plates.

Construction of E. coli α-hemolysin Based Secretion Systems

As described above, the hlyB and hlyD genes were introduced into the Gram-negative bacterial genome, harbouring a chromosomally encoded tolC gene, in order to enable the bacteria to express the complete α-hemolysin secretion apparatus. Proteins of interest were made competent for secretion via the α-hemolysin secretion system by the creation of gene fusions between the respective heterologous genes of interest and the C-terminal signal sequence of HlyA (hlyA$_s$). The gene fusions were cloned on suitable mobile vectors, such as plasmids or cosmids. Consecutively, they were introduced into a Gram negative bacterial strain which expresses the complete α-hemolysin secretion apparatus, consisting of HlyB, HlyD and TolC. The stable expression of the secretion system could be acchieved by insertion of the hlyB and hlyD genes into the bacterial chromosome. Alternatively, the hlyB and hlyD genes can be cloned on a mobile vector, e. g. plasmid, also encoding the heterologous proteins of interest as a fusion with the HlyA signal sequence, or the hlyB and hlyD genes and the fusion between the gene encoding the heterologous protein of interest and hlyA$_s$ can be cloned on separate, compatible plasmids.

In order to create an E. coli strain which stably expresses the α-hemolysin secretion apparatus, a 3.6 kb DNA fragment encoding the hlyB and hlyD genes was integrated into either of the chromosomal genes lacZ or recA gene of E. coli by the following cloning procedures:

Integration of hlyB and hlyD Into the Chromosomal lacZ Gene of E. coli Strain J53

The 9.5 kb plasmid pJRLacZins, (a kind gift of Joachim Reidl, University of Würzburg), was used as a vector plasmid. It is a λ-pir-dependent suicide plasmid based on the 6.3 kb plasmid pCVD442, conferring ampicillin resistance due to the presence of the bla gene and sensitiveness against growth in the presence of 5% sucrose at a gowth temperature of 30° C. due to the presence of the sacB gene. Consequently, plasmid pCVD442, the DNA sequence of which was provided by the company GATC, Konstanz, Germany, and its derivatives can only replicate in bacteria harbouring the λ-protein, such as in the E. coli K-12 strains Sy327 and Sm10λpir. Plasmid pJRLacZins, which contains an EcoRV restriction site within the lacZ sequence, was digested with the restriction enzyme EcoRV. Consecutively, a 3.6 kb DNA fragment containing the hlyB and hlyD genes was amplified by PCR from cosmid pCOS10, using the forward primer 5'-AAAAGCCCTTTTATGGATTCTTGTCAT-AAAATTGATTATGGG (SEQ ID NO: 24), designated Stu-HlyB1 (designed according to hemolysin-specific sequence with accession no. M14107), and the reverse primer 5'-AAAAGGCCTTTTTTAACGCTCACG-TAAACTTTCTGT (SEQ ID NO: 25), designated HlyD2Stu (designed according to hemolysin-specific sequence with accession no. M14107), and following restriction of the PCR product with StuI, ligated with the EcoRV restricted plasmid pJRLacZins to create the 13.1 kb plasmid pLacHlyBD. The plasmid encoded lacZ gene was destroyed during this cloning procedure. Plasmid pLacHlyBD allows the integration of the hlyBD genes into the chromosomal lacZ gene of any E. coli strain or other bacterial strain harbouring a homologous lacZ gene. The chromosomal lacZ gene in E. coli strains not possessing the ρ-protein, encoded by the pir gene, was destroyed following introduction of plasmid pLacHlyBD and a double-crossover event between the lacZ sequences on plasmid pLacHlyBD and the chromosomal lacZ gene, in consequence of which, the hlyB and hlyD genes were inserted into the chromosomal lacZ gene. LacZ-negative mutants were phenotypically screened by testing the resulting strains for growing as white colonies on agar plates containing Luria Bertani medium supplemented with 5% sucrose and X-Gal at 30° C. and for loss of ampicillin resistance. Genotypically, the mutants were tested by PCR analysis using the E. coli lacZ specific (accession no. V00296) forward primer lacZEV-up (5'-CTGCTGCTGCT-GAACGGCAAG) (SEQ ID NO: 31), and reverse primer lacZEV-down (5'-TCATTGGCACCATGCCGTGGG) (SEQ ID NO: 32). The PCR products received from the mutants differed from those of the wild-type lacZ-positive strains by size, resulting from the integration of the hlyB and hlyD sequences. Moreover, insertion of the hlyB and hlyD sequences into the chromosomal lacZ gene was assured by DNA sequencing.

Integration of hlyB and hlyD Into the Chromosomal RecA Gene of E. coli K-12 Strain J53

A 3.6 kb DNA fragment containing the hlyB and hlyD genes was amplified by PCR using the cosmid pCOS10 as a template and the forward primer Mibi-151 (5'-ATGGAT-TCTTGTCATAAAATTGATTATGGG) (SEQ ID NO: 1) and the reverse primer HlyD2 (5'-TTAACGCTCACG-TAAACTTTCTGT) (SEQ ID NO: 21), designed according to hemolysin-specific sequence of cosmid pCOS10 which was established by the company GATC, Konstanz, Germany), and accession no. M14107, respectively. The resulting 3.6 kb PCR product was ligated with the 3.5 kb EcoRV restricted plasmid vector pETBlue-1 which is commercially available from the company Novagen Calbiochem-Novabiochem, Bad Soden, Germany, resulting in the 7.1 kb plasmid pETBlue1-hlyBD. In consequence, expression of the hlyB and hlyD genes was under control of the IPTG-inducible T7 promoter.

PCR using plasmid pETBlue1-hlyBD as a template and the forward primer Mibi-169 (5'-CTAACCTGAC-CTAAAATTGTGAGCGCTCACAATTCTCGTGA) (SEQ ID NO: 2), designed according to pETBlue-1-hlyBD sequence, and the above described reverse primer HlyD2, resulted in a 3.9 kb PCR product, designated "Stop-lacO/T7 promoter-hlyBD" harbouring the hlyB and hlyD genes as well as stop codons and lacO/T7 promoter sequences upstream of hlyB.

PCR using the E. coli K-12 strain C600 as a template and the ygaD-specific forward primer Mibi-167 (5'-ATGACT-GACAGTGAACTGATGCAG) (SEQ ID NO: 3) and the oraA-specific reverse primer Mibi-168 (5'-TCAGTCG-GCAAAATTTCGCCAAATCTCC) (SEQ ID NO: 4), both designed according to accession no. AE000354, resulted in the amplification of a 2.2 kb DNA fragment harbouring the recA gene flanked upstream by ygaD and downstream by oraA sequences. Insertion of the resulting 2.2 kb PCR product into position 295 of the 3.9 kb plasmid vector pCR2.1-TOPO, which is commercially available from the company Invitrogen Corporation, resulted in the 6.1 kb plasmid pCR2.1-TOPO-ygaD-recA-oraA. Plasmid pCR2.1-TOPO-ygaD-recA-oraA was linerarized by digestion with the restriction enzyme AccI, which cuts at position 994 of the 2.2 kb ygaD-recA-oraA insert within the recA gene, and blunt-ended by treatment with Klenow fragment.

Ligation of the above described 3.9 kb PCR product "Stop-lacO/T7 promoter-hlyBD" with the above described AccI restricted 6.1 kb plasmid "pCR2.1-TOPO-ygaD-recA-oraA" resulted in the 10 kb plasmid "pCR2.1-ygaD-recA'-Stop-$P_{T7}$-hlyBD-recA''-oraA", which was consecutively digested with the restriction enzymes SacI and SphI, resulting in a 6.2 kb DNA fragment containing the 3.9 kb "Stop-lacO/T7 promoter-hlyBD" fragment flanked upstream by ygaD and recA specific sequences and downstream by recA and oraA specific sequences. Consecutively, this 6.2 kb DNA fragment was ligated with the SacI and SphI restricted above described 6.3 kb suicide vector plasmid pCVD442, resulting in the 12.5 kb plasmid pCVD442-$P_{T7}$-hlyBD.

Plasmid pCVD442-$P_{T7}$-hlyBD allowed the integration of the hlyBD genes unter control of the T7 promoter into the chromosomal recA gene of recA$_+$ E. coli strains. The chromosomal recA gene in E. coli strains not possessing the ρ-protein, encoded by the pir gene, was destroyed following introduction of plasmid pCVD442$P_{T7}$-hlyBD and a double-crossover event between the recA sequences on plasmid pCVD442-$P_{T7}$-hlyBD and the chromosomal recA gene, in consequence of which, the hlyB and hlyD genes were inserted into the chromosomal recA gene. RecA-negative mutants were phenotypically screened for by testing the resulting strains for their growth on agar plates containing Luria Bertani medium supplemented with 5% sucrose and X-Gal at 30° C., for loss of ampicillin resistance, as well as for sensitivity to UV light, mitomycin C and methyl-methanethiosulsfonate [Mühldorfer et al. (1996) Infect. Immun. 64:495–502]. Genotypically, the mutants were tested by PCR analysis using E. coli recA specific (accession no. AE000354) forward primer Mibi-224 (5'-CGCT-GACGCTGCAGGTGATCGCCG) (SEQ ID NO: 5) and reverse primer Mibi-225 (5'-TCCGGGTTACCGAACAT-CACACCA) (SEQ ID NO: 6) binding up- and downstream of the AccI site within the recA gene, respectively. The PCR products received from the mutants differ from those of the wild-type recA-positive strains by size, resulting from the integration of the hlyB and hlyD sequences. Moreover, insertion of the hlyB and hlyD sequences into the chromosomal recA gene was assured by DNA sequencing.

Construction of Plasmids Harbouring Fusions Between Genes Encoding a Protein of Interest and HlyA$_s$.

As mentioned above, proteins of interest were made competent for secretion via the α-hemolysin secretion system by creating gene fusions between the respective heterologous genes of interest and the C-terminal signal sequence of HlyA (hlyA$_s$). The gene fusions were cloned on suitable mobile vectors, such as plasmids or cosmids. Consecutively, they were introduced into a Gram negative bacterial strain which expresses the complete α-hemolysin secretion apparatus, consisting of HlyB, HlyD and TolC. In addition to the fusion between the gene of interest and hlyA$_s$, as an option, sequences encoding affinity tag and/or epitope tag and/or protease cleavage site may be included as described above.

The stable expression of the secretion system could be acchieved by insertion of the hlyB and hlyD genes into the bacterial chromosome. Alternatively, the hlyB and hlyD genes can be cloned on a mobile vector, e. g. plasmid, also encoding the heterologous proteins of interest as a fusion with the HlyA signal sequence. As another option, the hlyB and hlyD genes and the fusion between the gene encoding the heterologous protein of interest and hlyA$_s$ can be cloned on separate, compatible plasmids.

Plasmids harbouring fusions between hlyA$_s$ and various heterologous genes of interest, which are subsequently transformed into E. coli strains harbouring either chromosomal or plasmid located hlyBD as well as a chromosomal tolC gene, were constructed. Examples herefore are the plasmid constructs pUCHlyCA, pETBlue-1-HlyCA, pETBlue-1-PhoA-HlyAs and pETBlue-1-lacZ-HlyAs, which were created as follows:

A 3.6 kb DNA fragment was amplified by PCR using the forward primer StuHlyC4 (5'-AAAAGGCCTTTTAT-GAATATAAACAAACCATTAGAG) (SEQ ID NO: 22) and reverse primer HlyA3Stu (5'-AAAAGGCCTTTTTTAT-GCTGATGTGGTCAGGGTTATTGAG) (SEQ ID NO: 23), designed according to hemolysinspecific sequences with accession no. M14107 and StuI digestable sequences, and cosmid pCOS10 as a template. The resulting PCR product was digested with the restriction enzyme StuI and consecutively ligated with the SmaI digested plasmid vector pUC18 to create the 6.3 kb plasmid pUCHlyCA, harbouring the hlyC and hlyA genes.

A 3.6 kb DNA fragment was amplified by PCR using the forward primer Mibi-142 (5'-ATGAACAGAAACAATC-CATTAGAGGTTCTT) (SEQ ID NO: 7) and reverse primer Mibi-143 (5'-TTATGCTGATGCGGTCAAAGTTAT-TGAGTTCCG) (SEQ ID NO: 8), designed according to hemolysin-specific sequence of cosmid pCOS10 which was established by the company GATC, Konstanz, Germany). The resulting PCR product was ligated with the EcoRV digested 3.5 kb plasmid vector pETBlue-1 to create the 7.1 kb plasmid pETBlue-1-HlyCA, harbouring the hlyC and hlyA genes under control of the T7 promoter.

A 1.5 kb DNA fragment was amplified in a 3-step crossover PCR using E. coil as a template and the phoA specific forward primer Mibi-148 (5'-ATGCGGACACCA-GAAATGCCTGTTCTGGAA) (SEQ ID NO: 9) and the phoA specific reverse primer Mibi-226 (5'-TTTCAGC-CCCAGAGGGGCTTTCAT) (SEQ ID NO: 10) in the fist PCR, pCOS10 as a template and the phoA/hlyAs specific forward primer Mibi-149 (5'-AAAGCCGCTCTGGGGCT-GAAATCAACTTATGCAGACCTGGAT ) (SEQ ID NO: 11) and the reverse primer Mibi-145 (5'-TTATGCTGAT-GCGGTCAAAGTTATTGAGTT) (SEQ ID NO: 12) in the second PCR and the resulting PCR products from the first and second PCRs as templates and the primers Mibi-148 and Mibi-145 in the 3$^{rd}$ PCR. The respective primers were designed according to E. coli phoA (accession no. M29666 J04079) and hemolysin specific sequences of cosmid pCOS10 which was established by the company GATC, Konstanz, Germany). The resulting 1.5 kb PCR product from the third PCR was ligated with the EcoRV digested 3.5 kb plasmid vector pETBlue-1 to create the 5 kb plasmid pETBlue-1-PhoA-HlyAs, harbouring the phoA-hiyA$_s$ fusion under control of the T7 promoter.

A 3.2 kb DNA fragment was amplified in a 3-step crossover PCR using E. coil as a template and the lacZ specific forward primer Mibi-144 (5'-ATGACTATGATTA-CAGATTCACTGGCCGTC) (SEQ ID NO: 13) and the lacZ specific reverse primer Mibi-227 (TTTTTGACACCAGAC- CAACTGGTA) (SEQ ID NO: 14) in the fist PCR, pCOS10 as a template and the lacZ/hlyAs specific forward primer Mibi-146 (5'-CAGTTGGTCTGGTGTCAAAAATCAACT-TATGCAGACCTGGAT) (SEQ ID NO: 15) and the reverse primer Mibi-145 (5'-TTATGCTGATGCGGTCAAAGT-TATTGAGTT) (SEQ ID NO: 12) in the second PCR and the resulting PCR products from the first and second PCRs as templates and the primers Mibi-144 and Mibi-145 in the $3^{rd}$ PCR. The respective primers were designed according to *E. coli* lacZ (accession no. V00296) and hemolysin specific sequences of cosmid pCOS10 which was established by the company GATC, Konstanz, Germany). The resulting 3.2 kb PCR product from the third PCR was ligated with the EcoRV digested 3.5 kb plasmid vector pETBlue-1 to create the 6.7 kb plasmid pETBlue-1-LacZ-HlyAs, harbouring the lacZ-hlyA$_s$ fusion under control of the T7 promoter.

The 4.2 kb plasmid pTOPO-Thr-Myc-His-HlyA$_s$ was constructed as follows: The genes encoding thrombin, Myc-epitope and His-tag were amplified by PCR using the Invitrogen plasmid vector pBAD/Myc-HisA as a template and the primer ThromMycBAD (5'-CTGGTTCCGCGTG-GATCTGGGCCCGAACAAAAACTCATCTCA) (SEQ ID NO: 29) which harbours the 18 bp thrombin gene sequence as a forward primer, and the primer HispBAD (5'-TCAAT-GATGATGATGATGATGGTCGACGGC) (SEQ ID NO: 30) as a reverse primer. Cloning of the resulting 89 bp PCR product into the lacZ gene of the Invitrogen vector pCR2.1.-TOPO, results in the 4.0 kb plasmid pTOPO-Thr-Myc-His. Consecutively, a 213 bp DNA fragment containing hlyAs flanked by NsiI restrictable sequences were amplified using the primers Mibi-108 (5'-CCAATGCATTGGTTCTG-CAGTTGTCAACTTATGCAGACCTGG) (SEQ ID NO: 16) and Mibi-109 (5'-CCAATGCATTGGTTCTGCAGT-TGTTATGCTGATGCGGTCAAA) (SEQ ID NO: 17) and the cosmid pCOS10 as a template. Ligation of the resulting, NsiI restricted PCR product with the NsiI restricted vector pTOPO-Thr-Myc-His resulted in the final 4.2 kb plasmid construct pTOPO-Thr-Myc-His-HlyAs, containing sequences encoding thrombin, Myc-epitope, His-tag upstream of hlyAs and upstream of single KpnI and BamHI cloning sites which were used as integration sites for various genes of interest, e. g. hlyCA, lacZ, phoA.

Moreover, plasmids harbouring fusions between hlyA$_s$ and various heterologous genes of interest as well as the hlyB and hlyD genes, which were subsequently transformed into *E. coli* strains only harbouring the chromosomal tolC, were constructed. Examples herefore are the plasmid constructs pUCHlyCABD, pETBlue-1-PhoA-HlyAsBD and pETBlue-1-lacZ-HlyAsBD. As a control vector, pETBlue-1-HlyAsBD was also constructed.

Plasmid pUCHlyCABD was constructed as follows: A 7.2 kb DNA fragment was amplified by PCR using the forward primer Mibi-142 (5'-ATGAACAGAAACAATCCATTA-GAGGTTCTT) (SEQ ID NO: 7) and reverse primer HlyD2 (5'-TTAACGCTCACGTAAACTTTCTGT) (SEQ ID NO: 21), designed according to hemolysin-specific sequence of cosmid pCOS10 which was established by the company GATC, Konstanz, Germany). The resulting PCR product was ligated with the EcoRV digested 3.5 kb plasmid vector pETBlue-1 to create the 10.7 kb plasmid pETBlue-1-Hly-CABD, harbouring the hlyCABD operon under control of the T7 promoter.

Plasmid pETBlue-1-PhoA-HlyAsBD was constructed as follows: A 5.2 kb DNA fragment was amplified in a 3-step crossover PCR using *E. coli* as a template and the phoA specific forward primer Mibi-148 (5'-ATGCGGACACCA-GAAATGCCTGTTCTGGAA) (SEQ ID NO: 9) and the phoA specific reverse primer Mibi-226 (5'-TTTCAGC-CCCAGAGCGGCTTTCAT) (SEQ ID NO: 10) in the first PCR, pCOS10 as a template and the phoA/hlyAs specific forward primer Mibi-149 (5'-AAAGCCGCTCTGGGGCT-GAAATCAACTTATGCAGACCTGGAT) (SEQ ID NO: 11) and the reverse primer HlyD2 (5'-TTAACGCTCACG-TAAACTTTCTGT) (SEQ ID NO: 21) in the second PCR and the resulting PCR products from the first and second PCRs as templates and the primers Mibi-148 and HlyD2 in the $3^{rd}$ PCR. The respective primers were designed according to *E. coli* phoA (accession no. M29666 J04079) and hemolysin specific sequences of cosmid pCOS10 which was established by the company GATC, Konstanz, Germany). The resulting 5.2 kb PCR product from the third PCR was ligated with the EcoRV digested 3.5 kb plasmid vector pETBlue-1 to create the 8.7 kb plasmid pETBlue-1-PhoA-HlyAsBD, harbouring the phoA-hiyA$_s$BD fusion under control of the T7 promoter.

Plasmid pETBlue-1-LacZ-HlyAsBD was constructed as follows: A 6.9 kb DNA fragment was amplified in a 3-step crossover PCR using *E. coli* as a template and the lacZ specific forward primer Mibi-144 (5'-ATGACTATGATTA-CAGATTCACTGGCCGTC) (SEQ ID NO: 13) and the lacZ specific reverse primer Mibi-227 (5'-TTTTTGACACCA-GACCAACTGGTA) (SEQ ID NO: 14) in the fist PCR, pCOS10 as a template and the lacZ/hlyAs specific forward primer Mibi-146 (5'-CAGTTGGTCTGGTGTCAAAAAT-CAACTTATGCAGACCTGGAT) (SEQ ID NO: 15) and the reverse primer HlyD2 (5'-TTAACGCTCACG-TAAACTTTCTGT) (SEQ ID NO: 21) in the second PCR and the resulting PCR products from the first and second PCRs as templates and the primers Mibi-144 and HlyD2 in the $3^{rd}$ PCR. The respective primers were designed according to *E. coli* lacZ (accession no. V00296) and hemolysin specific sequences of cosmid pCOS10 which was established by the company GATC, Konstanz, Germany). The resulting 6.9 kb PCR product from the third PCR was ligated with the EcoRV digested 3.5 kb plasmid vector pETBlue-1 to create the 10.4 kb plasmid pETBlue-1-LacZ-HlyAsBD, harbouring the lacZ-hlyA$_s$BD fusion under control of the T7 promoter.

Plasmid pETBlue-1-HlyAsBD was constructed as follows: A 3.8 kb DNA fragment was amplified by PCR using the forward primer Mibi-228 (5'-TCAACTTATGCAGAC-CTGGATAAT) (SEQ ID NO: 18) and reverse primer HlyD2 (5'-TTAACGCTCACGTAAACTTTCTGT) (SEQ ID NO: 21), designed according to hemolysin-specific sequence of cosmid pCOS10 which was established by the company GATC, Konstanz, Germany). The resulting PCR product was ligated with the EcoRV digested 3.5 kb plasmid vector pETBlue-1 to create the 7.3 kb plasmid pETBlue-1-HlyAsBD, harbouring hlyAsBD under control of the T7 promoter.

Construction of *Pichia pastoris* α-factor Based Secretion Systems

The above described *P. pastoris* secretion system is used in a modified version for FunProTec. In analogy to the above described *E. coli* hemolysin secretion system, plasmids derived from the above mentioned invitrogen *Pichia pastoris* vectors are constructed, harbouring various genes of interest and optional various protease cleavage sites and tag sequences. Plasmids harbouring fusions between the α-factor signal sequence and various heterologous genes of interest are constructed using the Invitrogen plasmid vectors pPICZalpha.

Plasmid pPICZalpha-A-LacZ is constructed as follows: A 3.1 kb DNA fragment is amplified by PCR using E.coli as a template and the lacZ (accession no. NC 002655) specific forward primer Mibi-159 (5'-ATATATGGGGTACCACTAT-GATTACAGATTCACTGG) (SEQ ID NO: 19), lacking the initial start codon but harbouring a KpnI cleavable sequence, and the lacZ specific reverse primer Mibi-162 (5'-ATATAT-GCTCTAGATTTTTGACACCAGACCAACTG) (SEQ ID NO: 20), lacking the stop codon but harbouring a XbaI cleavable sequence. The KpnI and XbaI restricted 3.1 kb PCR product is ligated with the 3.6 kb KpnI and XbaI restricted Invitrogen plasmid pPICZalphaA, resulting in the 6.7 kb plasmid pPICZalpha-A-LacZ. Following the propagation of this shuttle plasmid in E. coli Top10 F', the α-factor signal sequence-lacZ fusion is integrated into the P. pastoris genome after transformation of plasmid pPICZalpha-A-LacZ into P. pastoris and a crossover event between the AOX1 sequences on plasmid pPTCZalpha-A-LacZ and the chromosomal AOX1 sequences.

Establishment of a Compartment System for the Preservation of Secreted Proteins

Double Filter Technique

As illustrated in FIG. 1, two filters with an appropriate pore size are placed on top of each other on a bacterial growth agar plate. The top filter has a pore diameter that prevents bacterial migration from the top to the lower filter, but allows flow of the secreted fusion proteins to the lower filter. It has a low protein binding capacity. in constrast, the lower filter has an optimal protein binding capacity, either by nature or as a consequence of being coated at certain spots with a component which is an optimal binding partner for a component of the protein fusion to be secreted by the bacteria growing on the top filter. Both filters allow the flow-through of nutrients and growth factors from the bacterial growth agar plate to the bacterial colonies growing on the top filter. The bacterial colonies expessing a hemolysin secretion apparatus will secrete HlyA$_s$-protein fusions that will diffuse onto the lower filter which they bind to.

The above described E. coli strains 536, its isogenic mutants 536–21 and 536–39–192, E. coli K-12 wt, JM109, DH1, LE392, W678, 35, J53, EN99, WK6, HB101, 5K, CC118, C600, MC1029, DH5α) are subjected to the double filter technology: Two Millipore filters are placed on top of each other on a bacterial growth agar plate. The top filter (hydrophilic Durapore membrane filter with a low protein binding capacity, provided by Millipore, Eschbom, Germany, order no. HVLP09050) has a pore diameter of 0,45 μm, preventing bacterial migration from the top to the lower filter, but allowing flow of the secreted fusion proteins to the lower filter. The Millipore MF membrane filter (order no. VCWP09025), consisting of a mixed ester of cellulose acetate and cellulose nitrate, and having an optimal protein binding capacity by its chemical nature, is chosen as the lower filter. Both filters allow the flow-through of nutrients and growth factors from the bacterial growth agar plate to the bacterial colonies growing on the top filter. The bacteria are picked onto the top filter and growth is allowed to occur for 3 hours at 37° C. Consecutively, the secreted proteins which bind to the lower filter are visualized by PonceauS staining. By this method, only protein secreted by E. coli 536 is detectable. In another experiment, the lower filter is placed onto a sheep blood agar plate. Following overnight incubation at room temperature, lysis is visable at spots which lay underneath the E. coli 536 secreted protein toxin (FIG. 3). In a further experiment, the E. coli strains 536, 536–21, J53(pUCHlyCA) and J53(pUC18) are subjected to the double filter system, in consequence of which the lower filter is removed following 3 hours of bacterial growth at 37° C. and placed onto a sheep blood agar plate. Following overnight incubation at room temperature, lysis is visable at spots which lay underneath the protein spots derived from E. coli 536 and J53(pUCHlyCA).

Stacked Microwells Technique

As described in FIG. 2, stacked microwell plates are used, consisting of microwells placed on top of each other and separated by a filter membrane with a pore diameter that prevents bacterial migration but allows flow of the secreted fusion proteins from the top well to the lower well. Liquid cultures of bacteria are growing in the upper microwell plate. Proteins secreted by those bacteria diffuse into the lower well, from which they can be harvested as a protein solution. In particular it is preferred that, a liquid culture of a bacterium expessing a hemolysin secretion apparatus secretes HlyA$_s$-protein fusions that diffuse into the lower well, from which it can be harvested as a protein solution. The "MultiScreen Assay System" provided by Millipore (Eschbom, Germany) and the Millipore MultiScreen filtration plates MAHVS4510 with 0,45 μm Durapore PVDF membranes and the Greiner Polyproyien-Microplates 651201 are used as the lower harvest plates in preliminary experiments. The above described E. coli strains 536, its isogenic mutants 536–21 and 536–39–192, E. coli K-12 wt, JM109, DH1, LE392, W678, 35, J53, EN99, WK6, HB101, 5K, CC118, C600, MC1029, subjected to the double filter technology. 20 μl of each of the protein solutions harvested from the lower plates are places onto Oxoid sheep blood agar plates. Only the protein secreted by E. coli 536 elicits hemolysis.

Determination of Protein Secretion of E. coli and Pichia pastoris Strains

Protein secretion of E. coli and Pichia pastoris strains can be tested following the application of the double filter technique, described above: Following binding to the lower filter in this system the secreted proteins can subsequently be subjected to standard protein detection methods, including ink, PonceauS, Coomassie or silver stains.

In case of the HlyA cytotoxin, its secretion can be monitored by its hemolytic activity of the sterile-filtered (using 0,45 μm filters) culture supematant on sheep blood agar plates.

Generally, in case of proteins with a known function, the filter-sterilized culture supernatants of the respective bacteria can be examined in functional assays.

EXAMPLES OF RESULTS OBTAINED WITH THE INVENTION

DNA Sequence of the Hemolysin Operon which is Located on the Pathogenicity Island I (Pai I) of E coli Strain 536

Cosmid pCOS10 [Knapp et al. (1986) J. Bacterdol. 168: 22–30] kindly provided by G. Blum-Oehler, University of Würzburg, contains Pai I of the uropathogenic E coli (UPEC) strain [Berger et al. (1982) J. Bacteriol. 152:1241–1247; Blum et al. (1994) Infect. Immun. 62:606–614; Hacker et al. (1983) J. Bacteriol. 154:11145–1154]). Following its Isolation from E. coli strain HB101(pCOS10) by the Quiagen protocoll, this cosmid was used as a template in PCRs with various primer sets to amplify overlapping fragments of the hemolysin operon located on pCOS10. The sequences of the primers were chosen from the DNA sequence of the hemolysin operon encoded by the *E. coli* plasmid pHly1 52, which was published by Hess et al., 1986, with accession no. M14107.

Hemolytic Activities of Various *E. coli* Strains

The uropathogenic *E. coli* strain 536, its isogenic mutant 536–21 which has lost the pathogenicity islands (Pais) I and II, each of which carries a hemolysin operon [Berger et al. (1982) J. Bacteriol. 152:1241–1247; Blum et al. (1994) Infect. Immun. 62:606–614; Hacker et al. (1983) J. Bacteriol. 154:11145–1154], *E. coli* KL320-HlyBD(pUCHlyCA) and various *E. coli* K-12 strains were compared for their hemolytic activities on sheep blood agar plates following overnight growth. Only the wild-type UPEC strain 536 and *E. coli* strain KL320-HlyBD(pUCHlyCA) but not the UPEC mutant 536–21 or any of the other *E. coli* K-12 strains elicited hemolysis of erythrocytes.

Double Filter Technology on Blood Agar Plate

UPEC strain 536, its mutant 536–21 as well as 15 *E. coli* K-12 strains and *E. coli* KL320-HlyBD (pUCHlyCA) were subjected to the double filter technology described above. The upper filter showed all the various *E. coli* colonies, the PonceauS treated lower filter only displayed stained dots underneath the filter spots of *E. coli* strain 536 and *E. coli* KL320-HlyBD(pUCHlyCA). The sheep blood agar underneath the double filter system also only showed hemolytic zones at spots which were localized underneath the filter carrying *E. coli* strain 536 and *E. coli* KL320-HlyBD (pUCHlyCA).

In another experiment, the lower filter was removed following 3 hours of bacterial growth at 37° C. and placed onto another sheep blood agar plate. Following overnight incubation at room temperature, lysis became again visable at spots which lay underneath the *E. coli* 536 and *E. coli* KL320HlyBD(pUCHlyCA) secreted protein toxin.

Figure 1:
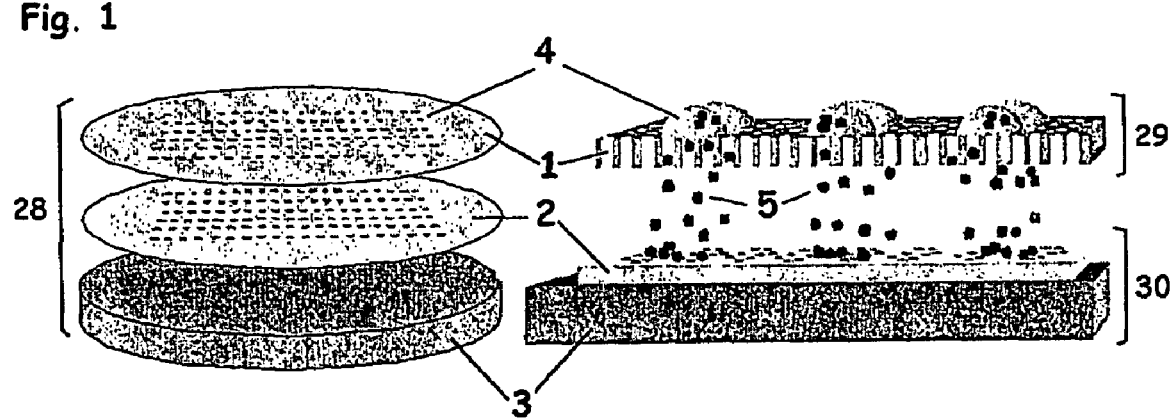
FIG. 1: Double filter technique. Two filters (1, 2) are placed on top of each other on a bacterial growth agar plate (3) forming a compartment system (28). Cells secreting proteins of interest (5) are growing on the top filter (1) in the form of single colonies (4) whereby the growing cells on the top filter (1) form a first compartment (29). A lower filter (2) and the bacterial growth agar plate (3) are forming a second compartment (30). The top filter (1) which is part of the first compartment functions as a barrier which barrier has a pore diameter that prevents bacterial migration from the top filter (1) to the lower filter (2), but allows flow of the secreted proteins of interest (5) to the lower filter (2), the latter of which is part of the second compartment (30) and has an optimal protein binding capacity. Both filters (1, 2) allow the flow-through of nutrients and growth factors from the bacterial growth agar plate (3) to the bacterial colonies (4) growing on the top filter (1). In the first compartment (29), growing bacterial cell colonies (4) have a discrete arrangement. Consequently, secreted proteins of interest (5) migrate through the top filter (1) onto the lower filter (2) of the second compartment (30) building an array of descrete protein spots.
Figure 2:
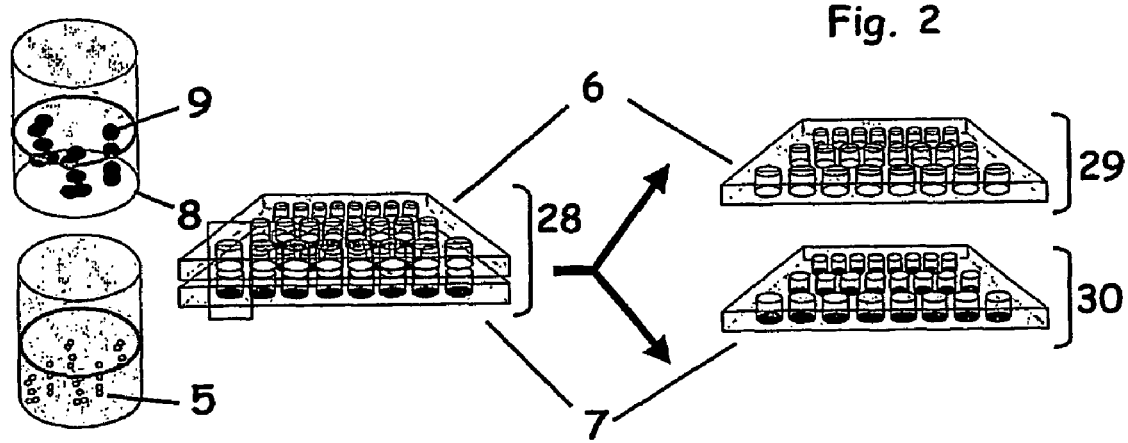
FIG. 2: Stacked mircowells technique. Two microtiter plates (6, 7) are placed on top of each other and separated by a filter membrane (8) forming a compartment system (28). A liquid culture of cells (9) growing in the wells of the top microliter plate (6) and the mebrane (8) are forming the first compartment (29) of the compartment system (28). The second compartment (30) is constituted by wells of the lower microtiter plate (7) in which proteins of interest (5) are secreted. The filter membrane (8) has a pore diameter that prevents bacterial migration but allows flow of the proteins of interest (5) from wells of the top microtiter plate (6) to the wells of the lower mlcrotiter plate (7). A liquid culture (9) of cells growing in the wells of the top microtiter plate (6) will secrete proteins of interest (5) which diffuse into wells of the lower microfiter plate (7), from which they are harvested.
Figure 3:
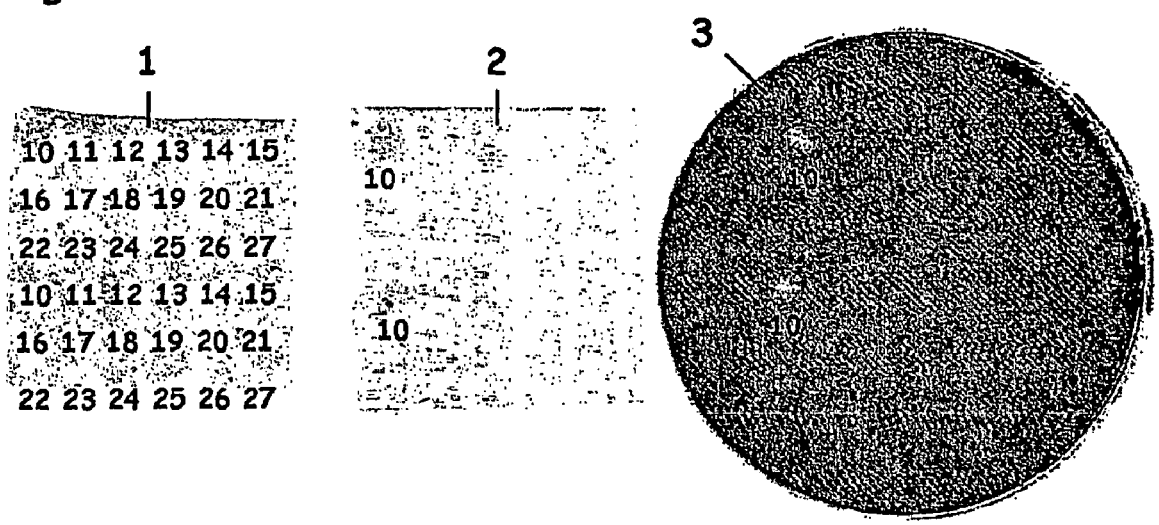
FIG. 3: Double filter system. The *E. coli* strains 536 (10), 536–21 (11), 536–39–192 (12), JM109 (14), DH1 (15), LE392 (16), W678 (17), 35 (18), J53 (19), EN99 (20), WK6 (21), HB101 (22), 5K (23), CC118 (24), C600 (25), MC1029 (26) and DH5Δ (27) are subjected to the double filter system.

Two Millipore filters (1,2) are placed on top of each other on a bacterial growth agar plate (3). The top filter (1) (hydrophilic Durapore membrane filter with a low protein binding capacity, provided by Millipore, Eschbom, Germany, order no. HVLP09050) has a pore diameter of 0,45 μm, preventing bacterial migration from the top to the lower filter (2), but allowing flow of the secreted fusion proteins to the lower filter (2). The Millipore MF membrane filter (order no. VCWP09025), consisting of a mixed ester of cellulose acetate and cellulose nitrate, and having an optimal protein binding capacity by its chemical nature, is used as the lower filter (2). Both filters (1,2) allow the flow-through of nutrients and growth factors from the bacterial growth agar plate (3) to the bacterial colonies growing on the top filter (1). The bacteria are picked onto the top filter and growth is allowed to occur for 3 hours at 370C. Consecutively, the lower filter (2) is removed following 3 hours of bacterial growth at 37° C. and placed onto a sheep blood agar plate. Following overnight incubation at room temperature, lysis is visable at spots which lay underneath the *E. coli* 536 secreted protein toxin.

TABLES

TABLE 1. Oligonucleotides used in the present application

| Oligonucleotide designation | nucleotide sequence | anneals to gene or plasmid position | strand |
|---|---|---|---|
| HlyD2 | 5'-TTA ACG CTC ACG TAA ACT TTC TGT-3' (SEQ ID NO:21) | hlyD/8044-8021*[1] | − |
| StuHlyC4 | 5'-AAA AGG CCT TTT ATG AAT ATA AAC AAA CCA TTA GAG-3' (SEQ ID NO: 22) | hlyC/796-819*[1] | + |
| HlyA3Stu | 5'-AAA AGG CCT TTT TTA TGC TGA TGT GGT CAG GGT TAT TGA G-3' (SEQ ID NO: 23) | hlyA/4394-4367*[1] | − |

TABLE 1. Oligonucleotides used in the present application

| Oligonucleotide designation | nucleotide sequence | anneals to gene or plasmid position | strand |
|---|---|---|---|
| StuHlyB1 | 5'-AAA AGG CCT TTT ATG GAT TCT TGT CAT AAA ATT GAT TAT GGG-3' (SEQ ID NO: 24) | hlyB/4466-4495*[1] | + |
| HlyD2Stu | 5'-AAA AGG CCT TTT TTA ACG CTC ACG TAA ACT TTC TGT-3' (SEQ ID NO: 25) | hlyD/8044-8021*[1] | − |
| XbaHlyA$_s$-up | 5'-CTA GTC TAG ACT ACT TAG CCT ATG AAG TCA GGG TGA TCT TAA-3' (SEQ ID NO: 26) | hlyA/4212-4239*[1] | + |
| XbaHlyA$_s$-down | 5'-CTA GTC TAG ACT AGT TAT GCT GAT GTG GTC AGG GTT ATT GAG-3' (SEQ ID NO: 27) | hlyA/4367-4394*[1] | − |
| XbaHlyA$_s$-linker | 5'-CTA GTC TAG ACT AGA GTT CTT TCC TCT TTA ACA TCG AAG C-3' (SEQ ID NO: 28) | hlyA/4285-4310*[1] | − |
| ThromMycBAD | 5'-CTG GTT CCG CGT GGA TCT GGG CCC GAA CAA AAA CTC ATC TCA-3' (SEQ ID NO: 29) | pBAD/Myc-HisA/372-395 | + |
| HispBAD | 5'-TCA ATG ATG ATG ATG ATG ATG GTC GAC GGC-3' (SEQ ID NO: 30) | pBAD/Myc-HisA/414-443 | − |
| lacZEV-up | 5'-CTG CTG CTG CTG AAC GGC AAG-3' (SEQ ID NO: 31) | E. coli-lacZ/1021-1041 | + |
| lacZEV-down | 5'-TCA TTG GCA CCA TGC CGT GGG-3' (SEQ ID NO: 32) | E. coli-lacZ/1250-1270 | − |

*[1] the numbers refer to the nucleotide positions of the 8215 bp nucleotide sequence of the E. coli plasmid pHly152 encoded hemolysin determinant published by Hess et al., 1986, with accession no. M14107. The hemolysin genes hlyC, hlyA, hlyB and hlyD within this sequence are located at the nucleotide positions 796 to 1308, 1320 to 4394, 4466 to 6589 and 6608 to 8044, respectively.

---

The invention claimed is:

1. A process for the production of at least one protein of interest comprising culturing a host cell in a compartment system, which host cell is stably expressing a secretion system and capable of secreting the heterologous protein of interest, wherein the protein of interest is secreted by the host cell by means of a secretion signal, and which compartment system has at least a first and a second compartment, and wherein the host cell is located in the first compartment, and wherein the first and second compartment are separated from each other by a barrier, wherein the barrier is permeable for the secreted protein of interest, but not permeable for the host cell.

2. The process according to claim 1, wherein the host cell is expressing a secretion system encoded on a mobile vector.

3. The process according to claim 2, wherein the mobile vector is either a plasmid or a cosmid.

4. The process according to claim 1, wherein the barrier is part of the first compartment of the compartment system.

5. The process according to claim 1, wherein the barrier is a membrane filter, which membrane filter has a pore diameter that prevents host cell migration and allows the diffusion of the secreted protein of interest through the membrane.

6. The process according to claim 1, wherein the first compartment is located above the second compartment and the secreted protein of interest will diffuse by means of gravity through the barrier from the first compartment to the second compartment.

7. The process according to claim 5, wherein the host cell is located on the surface of the filter and the second compartment is a solid phase attached to the opposite surface of the filter and which solid phase is capable of retaining the secreted protein after diffusion through the filter.

8. The process according to claim 1, wherein the host cell is either *E.coli* or *Pichia patoris*.

9. The process according to claim 1, wherein the secretion of the protein of interest is effected by growth of the host cell.

10. The process according to claim 5, wherein the first and second compartment are stack microwells which are separated by said filter.

11. The process according to claim 1, wherein the protein of interest is obtained in the second compartment.

12. The process according to claim 1, wherein the secreted protein of interest carries an affinity tag, an epitope tag and/or carries a protease cleavage site suitable for removal of secretion signal and/or tag sequences.

13. The process according to claim 1 for the production of several different proteins of interest, wherein each host cell secreting a respective protein of interest is located in a defined area of the first compartment and each of the secreted proteins of interest will migrate to a defined area of the second compartment or wherein each host cell secreting a respective protein of interest is located in different first compartments and each of the secreted proteins of interest will migrate to different second compartments.

14. A process for the production of an array of several different proteins of interest, comprising culturing host cells in a compartment system, which host cells are stably expressing a secretion system, wherein the proteins of interest are secreted by the host cell by means of secretion signals, which enables the host cells to secrete the respective heterologous protein of interest and which compartment system has at least a first and a second compartment and wherein the different host cells are arranged in the form of an array in said first compartment and wherein the first and second compartment are separated from each other by a barrier, wherein the barrier is permeable for the secreted proteins of interest, but not permeable for the host cell and wherein the secreted proteins of interest are received in the second compartment in the form of an array.

15. The process according to claim 14, wherein the barrier is part of the first compartment of the compartment system.

16. The process according to claim 14, wherein the array of proteins corresponds to the proteome of an organism of interest.

* * * * *

SEQUENCE LISTING

<160> NUMBER OF SEQ ID NOS: 32

<210> SEQ ID NO 1
<211> LENGTH: 30
<212> TYPE: DNA
<213> ORGANISM: Escherichia coli
<220> FEATURE:
<223> OTHER INFORMATION: oligonucleotide name: Mibi-151

<400> SEQUENCE: 1
atggattctt gtcataaaat tgattatggg        30

<210> SEQ ID NO 2
<211> LENGTH: 41
<212> TYPE: DNA
<213> ORGANISM: Artificial Sequence
<220> FEATURE:
<223> OTHER INFORMATION: oligonucleotide name: Mibi-169, chimeric
      oligonucleotide comprising E.coli sequence/Stop/pETBlue1
      vector-sequence

<400> SEQUENCE: 2
ctaacctgac ctaaaattgt gagcgctcac aattctcgtg a        41

```
<210> SEQ ID NO 3
<211> LENGTH: 24
<212> TYPE: DNA
<213> ORGANISM: Escherichia coli
<220> FEATURE:
<223> OTHER INFORMATION: oligonucleotide name: Mibi-167

<400> SEQUENCE: 3
atgactgaca gtgaactgat gcag                                              24

<210> SEQ ID NO 4
<211> LENGTH: 28
<212> TYPE: DNA
<213> ORGANISM: Escherichia coli
<220> FEATURE:
<223> OTHER INFORMATION: oligonucleotide name: Mibi-168

<400> SEQUENCE: 4
tcagtcggca aaatttcgcc aaatctcc                                          28

<210> SEQ ID NO 5
<211> LENGTH: 24
<212> TYPE: DNA
<213> ORGANISM: Escherichia coli
<220> FEATURE:
<223> OTHER INFORMATION: oligonucleotide name: Mibi-224

<400> SEQUENCE: 5
cgctgacgct gcaggtgatc gccg                                              24

<210> SEQ ID NO 6
<211> LENGTH: 24
<212> TYPE: DNA
<213> ORGANISM: Escherichia coli
<220> FEATURE:
<223> OTHER INFORMATION: oligonucleotide name: Mibi-225

<400> SEQUENCE: 6
tccgggttac cgaacatcac acca                                              24

<210> SEQ ID NO 7
<211> LENGTH: 30
<212> TYPE: DNA
<213> ORGANISM: Escherichia coli
<220> FEATURE:
<223> OTHER INFORMATION: oligonucleotide name: Mibi-142

<400> SEQUENCE: 7
atgaacagaa acaatccatt agaggttctt                                        30

<210> SEQ ID NO 8
<211> LENGTH: 33
<212> TYPE: DNA
<213> ORGANISM: Escherichia coli
<220> FEATURE:
<223> OTHER INFORMATION: oligonucleotide name: Mibi-143

<400> SEQUENCE: 8
ttatgctgat gcggtcaaag ttattgagtt ccg                                    33

<210> SEQ ID NO 9
<211> LENGTH: 30
<212> TYPE: DNA
<213> ORGANISM: Escherichia coli
<220> FEATURE:
<223> OTHER INFORMATION: oligonucleotide name: Mibi-148
```

```
<400> SEQUENCE: 9
atgcggacac cagaaatgcc tgttctggaa                                    30

<210> SEQ ID NO 10
<211> LENGTH: 24
<212> TYPE: DNA
<213> ORGANISM: Escherichia coli
<220> FEATURE:
<223> OTHER INFORMATION: oligonucleotide name: Mibi-226

<400> SEQUENCE: 10
tttcagcccc agagcggctt tcat                                          24

<210> SEQ ID NO 11
<211> LENGTH: 42
<212> TYPE: DNA
<213> ORGANISM: Escherichia coli
<220> FEATURE:
<223> OTHER INFORMATION: oligonucleotide name: Mibi-149

<400> SEQUENCE: 11
aaagccgctc tggggctgaa atcaacttat gcagacctgg at                      42

<210> SEQ ID NO 12
<211> LENGTH: 30
<212> TYPE: DNA
<213> ORGANISM: Escherichia coli
<220> FEATURE:
<223> OTHER INFORMATION: oligonucleotide name: Mibi-145

<400> SEQUENCE: 12
ttatgctgat gcggtcaaag ttattgagtt                                    30

<210> SEQ ID NO 13
<211> LENGTH: 30
<212> TYPE: DNA
<213> ORGANISM: Escherichia coli
<220> FEATURE:
<223> OTHER INFORMATION: oligonucleotide name: Mibi-144

<400> SEQUENCE: 13
atgactatga ttacagattc actggccgtc                                    30

<210> SEQ ID NO 14
<211> LENGTH: 24
<212> TYPE: DNA
<213> ORGANISM: Escherichia coli
<220> FEATURE:
<223> OTHER INFORMATION: oligonucleotide name: Mibi-227

<400> SEQUENCE: 14
tttttgacac cagaccaact ggta                                          24

<210> SEQ ID NO 15
<211> LENGTH: 42
<212> TYPE: DNA
<213> ORGANISM: Escherichia coli
<220> FEATURE:
<223> OTHER INFORMATION: oligonucleotide name: Mibi-146

<400> SEQUENCE: 15
cagttggtct ggtgtcaaaa atcaacttat gcagacctgg at                      42

<210> SEQ ID NO 16
<211> LENGTH: 42
```

```
<212> TYPE: DNA
<213> ORGANISM: Escherichia coli
<220> FEATURE:
<223> OTHER INFORMATION: oligonucleotide name: Mibi-108

<400> SEQUENCE: 16
ccaatgcatt ggttctgcag ttgtcaactt atgcagacct gg                              42

<210> SEQ ID NO 17
<211> LENGTH: 42
<212> TYPE: DNA
<213> ORGANISM: Escherichia coli
<220> FEATURE:
<223> OTHER INFORMATION: oligonucleotide name: Mibi-109

<400> SEQUENCE: 17
ccaatgcatt ggttctgcag ttgttatgct gatgcggtca aa                              42

<210> SEQ ID NO 18
<211> LENGTH: 24
<212> TYPE: DNA
<213> ORGANISM: Escherichia coli
<220> FEATURE:
<223> OTHER INFORMATION: oligonucleotide name: Mibi-228

<400> SEQUENCE: 18
tcaacttatg cagacctgga taat                                                  24

<210> SEQ ID NO 19
<211> LENGTH: 36
<212> TYPE: DNA
<213> ORGANISM: Artificial Sequence
<220> FEATURE:
<223> OTHER INFORMATION: oligonucleotide name: Mibi-159, chimeric
      oligonucleotide comprising E.coli sequence and a KpnI restriction
      endonuclease cleavage site

<400> SEQUENCE: 19
atatatgggg taccactatg attacagatt cactgg                                     36

<210> SEQ ID NO 20
<211> LENGTH: 35
<212> TYPE: DNA
<213> ORGANISM: Artificial Sequence
<220> FEATURE:
<223> OTHER INFORMATION: oligonucleotide name: Mibi-162, chimeric
      oligonucleotide comprising E.coli sequence and a XbaI restriction
      endonuclease cleavage site

<400> SEQUENCE: 20
atatatgctc tagattttg acaccagacc aactg                                       35

<210> SEQ ID NO 21
<211> LENGTH: 24
<212> TYPE: DNA
<213> ORGANISM: Escherichia coli
<220> FEATURE:
<223> OTHER INFORMATION: oligonucleotide name: HlyD2

<400> SEQUENCE: 21
ttaacgctca cgtaaacttt ctgt                                                  24

<210> SEQ ID NO 22
<211> LENGTH: 36
<212> TYPE: DNA
<213> ORGANISM: Artificial Sequence
<220> FEATURE:
```

<223> OTHER INFORMATION: oligonucleotide name: StuHlyC4, chimeric
oligonucleotide comprising E.coli sequence and a StuI restriction
endonuclease cleavage site

<400> SEQUENCE: 22
aaaaggcctt ttatgaatat aaacaaacca ttagag                36

<210> SEQ ID NO 23
<211> LENGTH: 40
<212> TYPE: DNA
<213> ORGANISM: Artificial Sequence
<220> FEATURE:
<223> OTHER INFORMATION: oligonucleotide name: HlyA3Stu, chimeric
oligonucleotide comprising E.coli sequence and a StuI restriction
endonuclease cleavage site

<400> SEQUENCE: 23
aaaaggcctt ttttatgctg atgtggtcag ggttattgag                40

<210> SEQ ID NO 24
<211> LENGTH: 42
<212> TYPE: DNA
<213> ORGANISM: Artificial Sequence
<220> FEATURE:
<223> OTHER INFORMATION: oligonucleotide name: StuHlyB1, chimeric
oligonucleotide comprising E.coli sequence and a StuI restriction
endonuclease cleavage site

<400> SEQUENCE: 24 aaaagcccdtt ttatggattc ttgtcataaa attgattatg gg                42

<210> SEQ ID NO 25
<211> LENGTH: 36
<212> TYPE: DNA
<213> ORGANISM: Artificial Sequence
<220> FEATURE:
<223> OTHER INFORMATION: oligonucleotide name: HlyD2Stu, chimeric
oligonucleotide comprising E.coli sequence and a StuI restriction
endonuclease cleavage site

<400> SEQUENCE: 25
aaaaggcctt ttttaacgct cacgtaaact ttctgt                36

<210> SEQ ID NO 26
<211> LENGTH: 42
<212> TYPE: DNA
<213> ORGANISM: Artificial Sequence
<220> FEATURE:
<223> OTHER INFORMATION: oligonucleotide name: XbaHlyAs-up, chimeric
oligonucleotide comprising E.coli sequence and a XbaI restriction
endonuclease cleavage site

<400> SEQUENCE: 26
ctagtctaga ctacttagcc tatggaagtc agggtgatct ta                42

<210> SEQ ID NO 27
<211> LENGTH: 42
<212> TYPE: DNA
<213> ORGANISM: Artificial Sequence
<220> FEATURE:
<223> OTHER INFORMATION: oligonucleotide name: XbaHlyAs-down, chimeric
oligonucleotide comprising E.coli sequence and a XbaI restriction
endonuclease cleavage site

<400> SEQUENCE: 27
ctagtctaga ctagttatgc tgatgtggtc agggttattg ag                42

-continued

```
<210> SEQ ID NO 28
<211> LENGTH: 40
<212> TYPE: DNA
<213> ORGANISM: Escherichia coli
<220> FEATURE:
<223> OTHER INFORMATION: oligonucleotide name: XbaHlyAs-linker

<400> SEQUENCE: 28
ctagtctaga ctagagttct ttcctcttta acatcgaagc                           40

<210> SEQ ID NO 29
<211> LENGTH: 42
<212> TYPE: DNA
<213> ORGANISM: Artificial Sequence
<220> FEATURE:
<223> OTHER INFORMATION: oligonucleotide name: ThromMycBAD, chimeric
      oligonucleotide comprising a part of the human thrombin sequence,
      a linker sequence, and a sequence of the vector pBAD/Myc-HisA
      (Invitrogen)

<400> SEQUENCE: 29
ctggttccgc gtggatctgg gcccgaacaa aaactcatct ca                        42

<210> SEQ ID NO 30
<211> LENGTH: 30
<212> TYPE: DNA
<213> ORGANISM: Artificial Sequence
<220> FEATURE:
<223> OTHER INFORMATION: oligonucleotide name: HispBAD, sequence derived
      from vector pBAD/Myc-HisA (Invitrogen)

<400> SEQUENCE: 30
tcaatgatga tgatgatgat ggtcgacggc                                      30

<210> SEQ ID NO 31
<211> LENGTH: 21
<212> TYPE: DNA
<213> ORGANISM: Escherichia coli
<220> FEATURE:
<223> OTHER INFORMATION: oligonucleotide name: lacZEV-up

<400> SEQUENCE: 31
ctgctgctgc tgaacggcaa g                                               21

<210> SEQ ID NO 32
<211> LENGTH: 21
<212> TYPE: DNA
<213> ORGANISM: Escherichia coli
<220> FEATURE:
<223> OTHER INFORMATION: oligonucleotide name: lacZEV-down

<400> SEQUENCE: 32
tcattggcac catgccgtgg g                                               21
```